United States Patent
Amarasinghe et al.

(10) Patent No.: US 10,335,568 B2
(45) Date of Patent: Jul. 2, 2019

(54) NECK STRAP, CROWN STRAP ASSEMBLY AND HEADGEAR FOR A BREATHING MASK

(71) Applicant: RESMED LIMITED, Bella Vista, New South Wales (AU)

(72) Inventors: Amal Shirley Amarasinghe, Sydney (AU); Jessica Lea Dunn, Sydney (AU); Justin John Formica, Sydney (AU); Christopher Scott Skipper, Sydney (AU)

(73) Assignee: ResMed Limited, Bella Vista (AU)

( * ) Notice: Subject to any disclaimer, the term of this patent is extended or adjusted under 35 U.S.C. 154(b) by 589 days.

(21) Appl. No.: 14/783,941

(22) PCT Filed: Apr. 9, 2014

(86) PCT No.: PCT/AU2014/000379
§ 371 (c)(1),
(2) Date: Oct. 12, 2015

(87) PCT Pub. No.: WO2014/165906
PCT Pub. Date: Oct. 16, 2014

(65) Prior Publication Data
US 2016/0045700 A1 Feb. 18, 2016

(30) Foreign Application Priority Data
Apr. 12, 2013 (EP) .................... 13163546

(51) Int. Cl.
*A61M 16/06* (2006.01)
*A61M 16/16* (2006.01)
(Continued)

(52) U.S. Cl.
CPC ...... *A61M 16/0683* (2013.01); *A61M 16/009* (2013.01); *A61M 16/0057* (2013.01);
(Continued)

(58) Field of Classification Search
CPC .................................................. A61M 16/0683
See application file for complete search history.

(56) References Cited

U.S. PATENT DOCUMENTS

| 4,703,879 A | 11/1987 | Kastendieck et al. |
| 4,782,832 A | 11/1988 | Trimble et al. |

(Continued)

FOREIGN PATENT DOCUMENTS

| CN | 101214402 A | 7/2008 |
| CN | 102014999 A | 4/2011 |

(Continued)

OTHER PUBLICATIONS

Further Examination Report issued in corresponding New Zealand Application No. 623462 dated Dec. 14, 2015.
(Continued)

*Primary Examiner* — Valerie L Woodward
(74) *Attorney, Agent, or Firm* — Nixon & Vanderhye P.C.

(57) ABSTRACT

A neck strap for a headgear includes a one-piece main body adapted to engage a patient's neck, first and second lower connection portions adapted to connect to respective first and second lower mask connection straps, and first and second upper connection portions adapted to connect to respective first and second lateral crown straps.

17 Claims, 27 Drawing Sheets

(51) Int. Cl.
  *A61M 16/20* (2006.01)
  *A61M 16/00* (2006.01)
  *A61M 16/08* (2006.01)
  *A61M 16/10* (2006.01)

(52) U.S. Cl.
  CPC ........ *A61M 16/06* (2013.01); *A61M 16/0616* (2014.02); *A61M 16/0666* (2013.01); *A61M 16/0069* (2014.02); *A61M 16/0633* (2014.02); *A61M 16/0825* (2014.02); *A61M 16/0858* (2014.02); *A61M 16/107* (2014.02); *A61M 16/16* (2013.01); *A61M 16/208* (2013.01); *A61M 2016/0027* (2013.01); *A61M 2016/0039* (2013.01); *A61M 2205/21* (2013.01); *A61M 2205/42* (2013.01); *A61M 2205/7545* (2013.01)

(56) References Cited

U.S. PATENT DOCUMENTS

| | | | |
|---|---|---|---|
| 4,944,310 | A | 7/1990 | Sullivan |
| 6,532,959 | B1 | 3/2003 | Berthon-Jones |
| 6,581,594 | B1 | 6/2003 | Drew et al. |
| 6,805,117 | B1* | 10/2004 | Ho ............ A61M 16/0683 128/201.22 |
| 7,296,575 | B1 | 11/2007 | Radney |
| 7,779,832 | B1* | 8/2010 | Ho ............ A61M 16/0683 128/201.22 |
| 7,866,944 | B2 | 1/2011 | Kenyon et al. |
| 8,522,784 | B2* | 9/2013 | Ng ............ A61M 16/06 128/205.25 |
| 8,636,479 | B2 | 1/2014 | Kenyon et al. |
| 8,638,014 | B2 | 1/2014 | Sears et al. |
| 2004/0067333 | A1* | 4/2004 | Amarasinghe .... A61M 16/0683 428/99 |
| 2006/0283461 | A1 | 12/2006 | Lubke et al. |
| 2007/0130663 | A1* | 6/2007 | Lang ............ A61M 16/0683 2/9 |
| 2008/0190432 | A1 | 8/2008 | Blochlinger et al. |
| 2009/0044808 | A1 | 2/2009 | Guney et al. |
| 2009/0050156 | A1 | 2/2009 | Ng et al. |
| 2009/0178680 | A1* | 7/2009 | Chang ............ A61M 16/0683 128/206.27 |
| 2010/0000534 | A1 | 1/2010 | Kooij et al. |
| 2011/0023874 | A1 | 2/2011 | Bath et al. |
| 2011/0197341 | A1* | 8/2011 | Formica ............ A61M 16/0683 2/209.3 |
| 2012/0145157 | A1 | 6/2012 | Lang et al. |

FOREIGN PATENT DOCUMENTS

| | | |
|---|---|---|
| CN | 102245250 A | 11/2011 |
| FR | 2977164 A1 | 1/2013 |
| GB | 2 358 787 A | 8/2001 |
| JP | 10-314307 | 12/1998 |
| JP | 10-314307 A | 12/1998 |
| JP | 2007-510486 | 4/2007 |
| JP | 2007-510486 A | 4/2007 |
| JP | 2010-509942 | 4/2010 |
| JP | 2010-509942 A | 4/2010 |
| JP | 2011-512967 | 4/2011 |
| JP | 2011-512967 A | 4/2011 |
| WO | WO 1998/004310 | 2/1998 |
| WO | WO 1998/034665 | 8/1998 |
| WO | WO 2000/078381 | 12/2000 |
| WO | WO 2004/073778 | 9/2004 |
| WO | WO 2005/063328 | 7/2005 |
| WO | WO 2006/012870 A1 | 2/2006 |
| WO | WO 2006/074513 | 7/2006 |
| WO | WO 2006/130903 | 12/2006 |
| WO | WO 2009/052560 | 4/2009 |
| WO | WO 2009/108995 | 9/2009 |
| WO | WO 2010/135785 | 12/2010 |
| WO | WO 2012/140514 | 10/2012 |
| WO | WO 2012/171072 | 12/2012 |
| WO | WO 2013/020167 | 2/2013 |
| WO | WO 2013/026092 | 2/2013 |
| WO | WO 2013/050920 | 4/2013 |
| WO | WO 2013/066195 A1 | 5/2013 |
| WO | WO 2014/110622 A1 | 7/2014 |
| WO | WO 2014/165906 | 10/2014 |

OTHER PUBLICATIONS

First Examination Report issued in corresponding New Zealand Application No. 714593 dated Dec. 14, 2015.
Patent Examination Report No. 1 issued in corresponding Australian Patent Application No. 2014252758 dated Jun. 2, 2016.
Sep. 14, 2016 Extended European Search Report issued in European Application No. 14782857.8.
First Office Action dated Oct. 9, 2016 issued in Chinese Application No. 201480033970.X with English translation (13 pages).
Second Examination Report dated Mar. 29, 2017 issued in Australian Application No. 2014252758 (4 pages).
Office Action dated Apr. 25, 2017 issued in European Application No. 14782857.8 (9 pages).
First Examination Report dated Jun. 6, 2017 issued in New Zealand Application No. 731995 (3 pages).
Further Examination Report dated Jun. 6, 2017 issued in New Zealand Application No. 714593 (2 pages).
Office Action dated Jul. 3, 2017 issued in Chinese Application No. 201480033970.X with English translation (6 pages).
Notice of Reasons for Rejection dated Nov. 6, 2017 issued in Japanese Application No. 2016-506727 with English translation (7 pages).
Communication Regarding Extension of Time Granted dated Dec. 22, 2017 issued in New Zealand Application No. 714593 (1 page).
Notice of Opposition to Grant of Patent (Section 21) filed by Fisher & Paykel Healthcare Limited on Dec. 21, 2017 in New Zealand Application No. 714593 (2 pages).
Application under Regulation 168 for Extension of Time filed by Fisher & Paykel Healthcare Limited on Dec. 21, 2017 in New Zealand Application No. 714593 (1 page).
Deadline for Counterstatement dated Mar. 8, 2018 issued in New Zealand Application No. 714593 (2 pages).
First Amended Notice of Opposition to Grant of Patent (Section 21), with no markups, dated Feb. 25, 2018 filed by Fisher & Paykel Healthcare Limited in New Zealand Application No. 714593 (2 pages).
First Amended Notice of Opposition to Grant of Patent (Section 21), with markups, dated Feb. 25, 2018 filed by Fisher & Paykel Healthcare Limited in New Zealand Application No. 714593 (2 pages).
Statement of Case dated Feb. 25, 2018 filed by Fisher & Paykel Healthcare Limited in New Zealand Application No. 714593 (39 pages).
Weinmann Medical Technology, "JOYCE Full Face—Full Face Mask with Unique Modular System", Feb. 2013.
"Respiratory Physiology", by John B. West, Lippincott Williams & Wilkins, $9^{th}$ edition published 2011.
International Search Report issued in PCT Application No. PCT/AU2014/000379 dated Aug. 11, 2014.
Written Opinion issued in PCT Application No. PCT/AU2014/000379 dated Aug. 11, 2014.
First Examination Report issued in related New Zealand Application No. 623462 dated Apr. 9, 2014.
Further Examination Report issued in related New Zealand Application No. 623462 dated Jun. 2, 2015.
New Zealand Application No. 623462 filed Apr. 7, 2014.
International Preliminary Report on Patentability issued in PCT Application No. PCT/AU2014/000379 dated Oct. 13, 2015.
Office Action dated May 18, 2018 issued in European Application No. 14782857.8 (8 pages).
Notice of Allowance dated Sep. 21, 2018 issued in Japanese Application No. 2016-506727 with English translation (6 pages).

(56) References Cited

OTHER PUBLICATIONS

Office Action dated Jun. 11, 2018 issued in Japanese Application No. 2016-506727 with English translation (6 pages).
Proceeding Correspondence dated Aug. 7, 2018 issued in New Zealand Application No. 714593 (2 pages).
Letter dated Jun. 27, 2018 filed by AJ Park in New Zealand Application No. 714593 (2 pages).

* cited by examiner

Copyright 2012 ResMed Limited

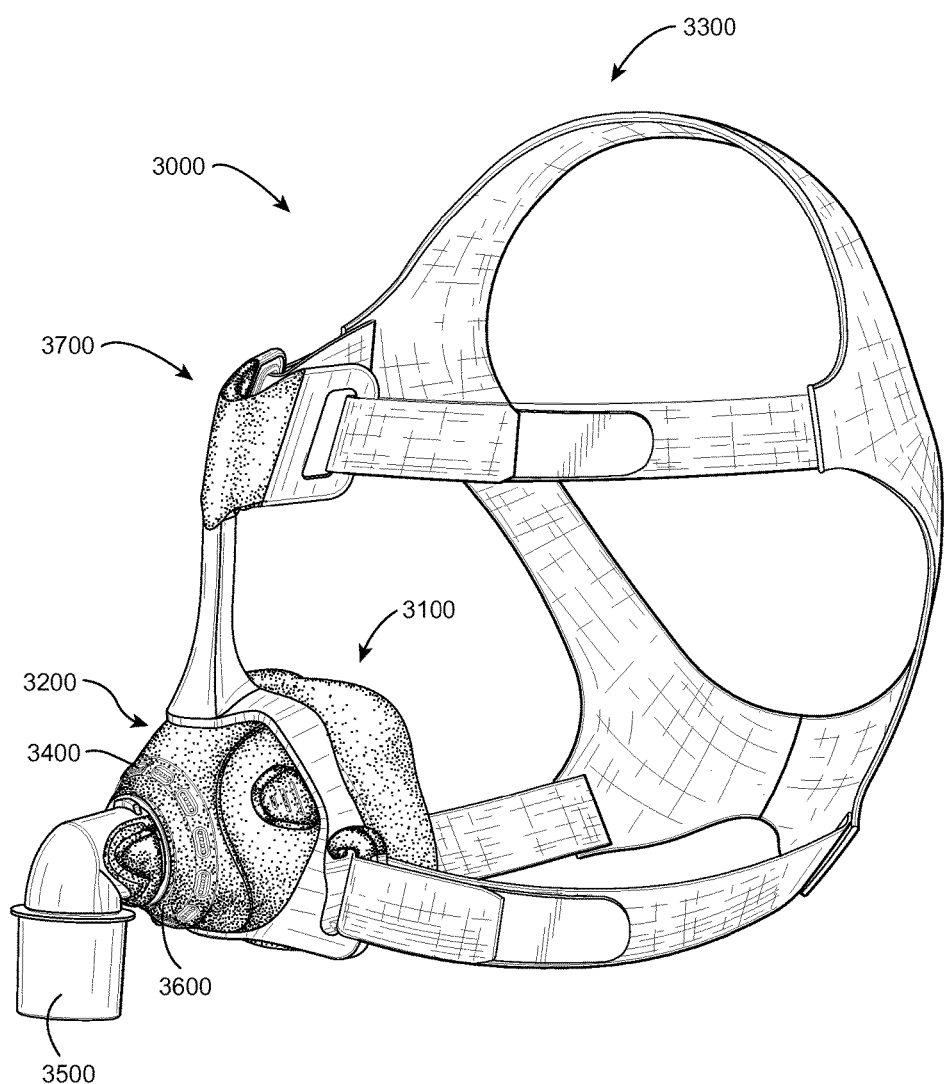
Fig. 4a (State of the art)

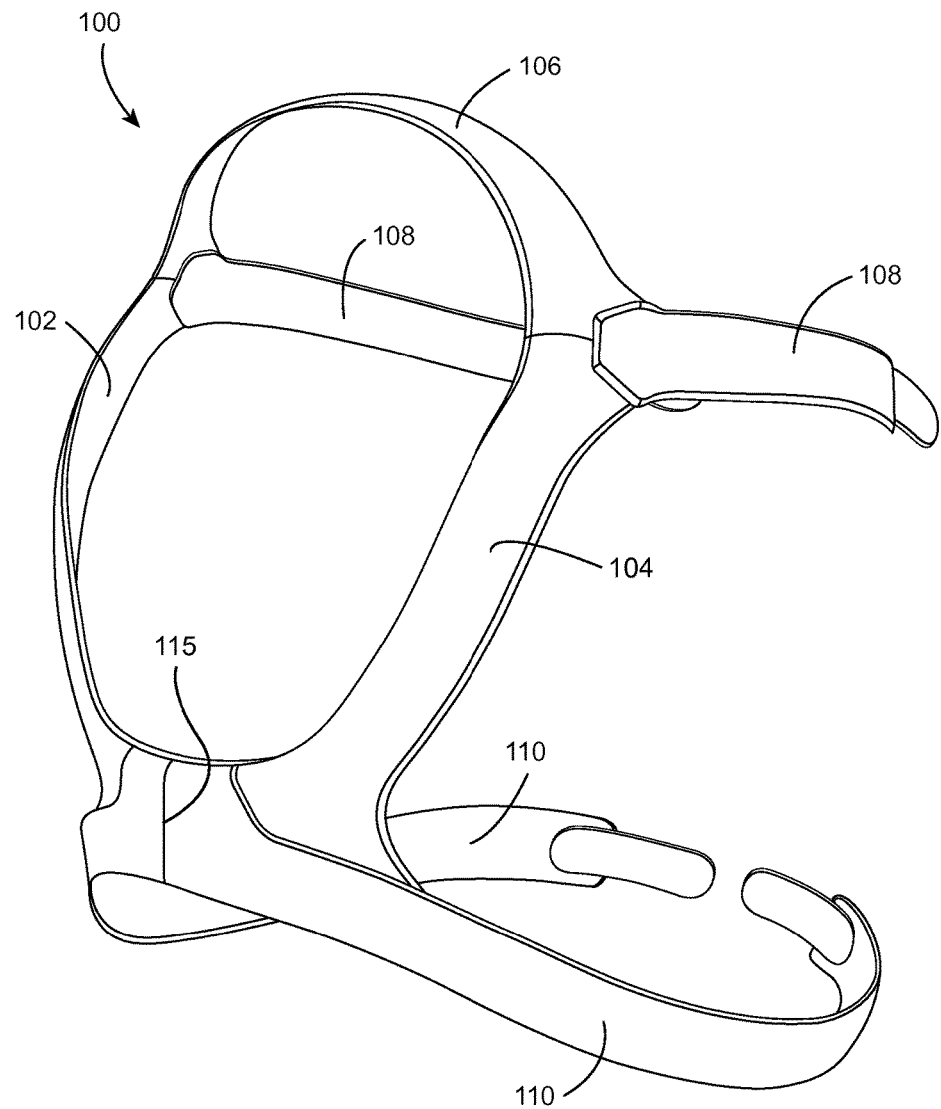
Fig. 4b (State of the art)

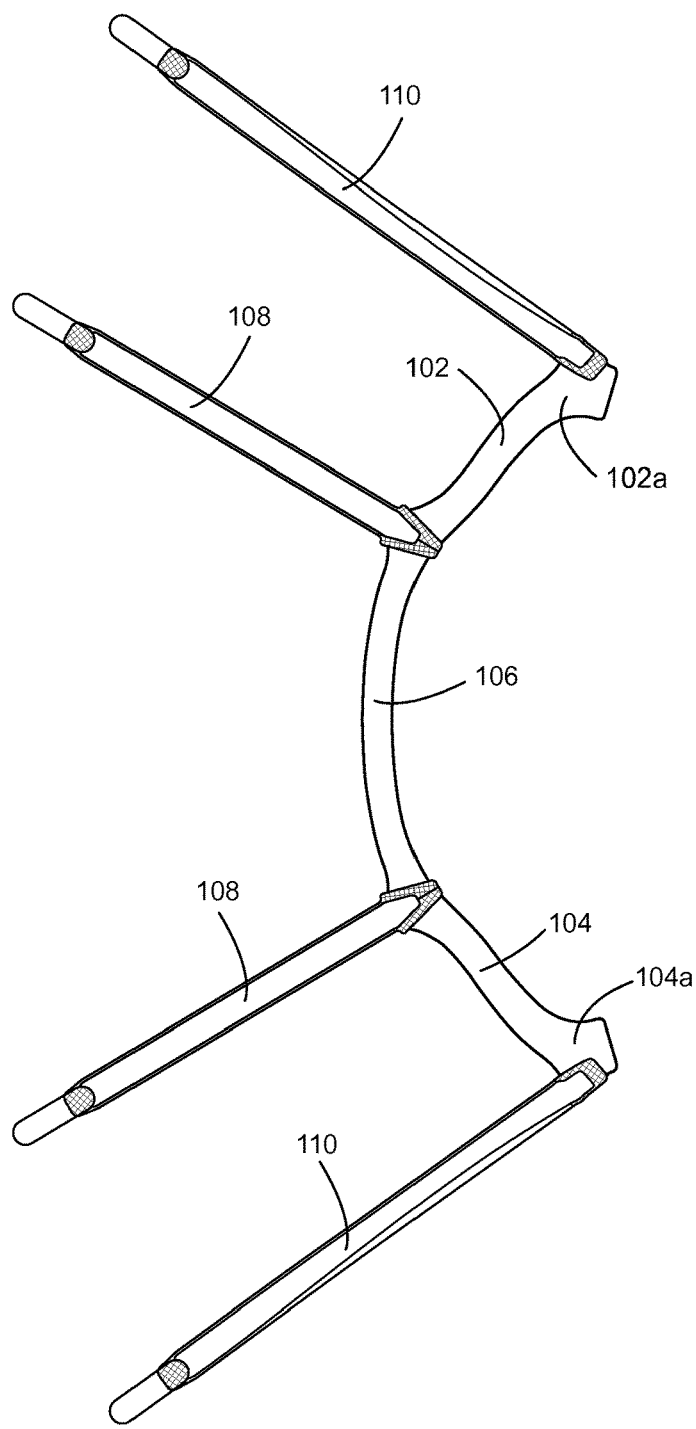
Fig. 4c (State of the art)

NECK STRAP, CROWN STRAP ASSEMBLY AND HEADGEAR FOR A BREATHING MASK

1. CROSS-REFERENCE TO RELATED APPLICATIONS

This application is the U.S. national phase of International Application No. PCT/AU2014/000379, filed Apr. 9, 2014, which designated the U.S. and claims priority from European Application No. EP 13163546.8, filed Apr. 12, 2013, the entire contents of each of which are incorporated herein by reference.

2. BACKGROUND OF THE TECHNOLOGY 2.1 Field of the Technology

The present technology relates to one or more of the detection, diagnosis, treatment, prevention and amelioration of respiratory-related disorders. In particular, the present technology relates to medical devices or apparatus, and their use.

More particularly, the present technology relates to a neck strap, a crown strap assembly and a headgear, e.g., for a patient interface, e.g., breathing mask, for instance used in a Positive Airway Pressure (PAP) therapy.

2.2 Description of the Related Art 2.2.1 Human Respiratory System and its Disorders The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the air into the venous blood and carbon dioxide to move out. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See West, Respiratory Physiology—the essentials.

A range of respiratory disorders exist.

Obstructive Sleep Apnea (OSA), a form of Sleep Disordered Breathing (SDB), is characterized by occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is a disorder of a patient's respiratory controller in which there are rhythmic alternating periods of waxing and waning ventilation, causing repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production.

Neuromuscular Disease (NMD) is a broad term that encompasses many diseases and ailments that impair the functioning of the muscles either directly via intrinsic muscle pathology, or indirectly via nerve pathology. Some NMD patients are characterised by progressive muscular impairment leading to loss of ambulation, being wheelchair-bound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g. Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g. Limb girdle, Facioscapulohumeral and Myotonic muscular dystrophy). Symptoms of respiratory failure in NMD include: increasing generalised weakness, dysphagia, dyspnea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterised by a restrictive defect and share the potential of long term hypercapnic respiratory failure. Scoliosis and/or kyphoscoliosis may cause severe respiratory failure. Symptoms of respiratory failure include: dyspnea on exertion, peripheral oedema, orthopnea, repeated chest infections, morning headaches, fatigue, poor sleep quality and loss of appetite.

Otherwise healthy individuals may take advantage of systems and devices to prevent respiratory disorders from arising.

2.2.2 Therapy

Nasal Continuous Positive Airway Pressure (CPAP) therapy has been used to treat Obstructive Sleep Apnea (OSA). The hypothesis is that continuous positive airway pressure acts as a pneumatic splint and may prevent upper airway occlusion by pushing the soft palate and tongue forward and away from the posterior oropharyngeal wall.

Non-invasive ventilation (NIV) provides ventilator support to a patient through the upper airways to assist the patient in taking a full breath and/or maintain adequate oxygen levels in the body by doing some or all of the work of breathing. The ventilator support is provided via a patient interface. NIV has been used to treat CSR, OHIS, COPD, MD and Chest Wall disorders.

Invasive ventilation (IV) provides ventilatory support to patients that are no longer able to effectively breathe themselves and is provided using a tracheostomy tube.

Ventilators may control the timing and pressure of breaths pumped into the patient and monitor the breaths taken by the patient. The methods of control and monitoring patients typically include volume-cycled and pressure-cycled methods. The volume-cycled methods may include among others, Pressure-Regulated Volume Control (PRVC), Volume Ventilation (VV), and Volume Controlled Continuous Mandatory Ventilation (VC-CMV) techniques. The pressure-cycled methods may involve, among others, Assist Control (AC). Synchronized Intermittent Mandatory Ventilation (SIMV), Controlled Mechanical Ventilation (CMV), Pressure Support Ventilation (PSV), Continuous Positive Airway Pressure (CPAP), or Positive End Expiratory Pressure (PEEP) techniques.

2.2.3 Systems

One known device used for treating sleep disordered breathing is the S9 Sleep Therapy System, manufactured by ResMed. Ventilators such as the ResMed Stellar™ Series of Adult and Paediatric Ventilators may provide support for invasive and non-invasive non-dependent ventilation for a range of patients for treating a number of conditions such as but not limited to NMD, OHS and COPD.

The ResMed Eliséc™ 150 ventilator and ResMed VS II™ ventilator may provide support for invasive and non-invasive dependent ventilation suitable for adult or paediatric patients for treating a number of conditions. These ventilators provide volumetric and barometric ventilation modes with a single or double limb circuit.

A system may comprise a PAP Device/ventilator, an air circuit, a humidifier, a patient interface, and data management.

2.2.4 Patient Interface

A patient interface may be used to interface respiratory equipment to its user, for example by providing a flow of breathable gas. The flow of breathable gas may be provided via a mask to the nose and/or mouth, a tube to the mouth or a tracheostomy tube to the trachea of the user. Depending upon the therapy to be applied, the patient interface may form a seal, e.g. with a face region of the patient, to facilitate the delivery of gas at a pressure at sufficient variance with ambient pressure to effect therapy. e.g. a positive pressure of about 10 cmH2O. For other forms of therapy, such as the delivery of oxygen, the patient interface may not include a seal sufficient to facilitate delivery to the airways of a supply of gas at a positive pressure of about 10 cmH2O.

The design of a patient interface presents a number of challenges. The face has a complex three-dimensional shape. The size and shape of noses varies considerably between individuals. Since the head includes bone, cartilage and soft tissue, different regions of the face respond differently to mechanical forces. The jaw or mandible may move relative to other bones of the skull. The whole head may move during the course of a period of respiratory therapy.

As a consequence of these challenges, some masks suffer from being one or more of obtrusive, aesthetically undesirable, costly, poorly fitting, difficult to use, and uncomfortable especially when worn for long periods of time or when a patient is unfamiliar with a system. For example, masks designed solely for aviators, mask designed as part of personal protection equipment, or for the administration of anaesthetics may be tolerable for their original application, but nevertheless be undesirably uncomfortable to be worn for extended periods of time. This is even more so if the mask is to be worn during sleep.

2.2.4.1 Seal-Forming Portion

Patient interfaces may include a seal-forming portion.

A patient interface may be partly characterised according to the design intent of where the seal-forming portion is to engage with the face in use. In one form of patient interface, a seal-forming portion may comprise two sub-portions to engage with respective left and right nares. In one form of patient interface, a seal-forming portion may comprise a single element that surrounds both nares in use. Such single element may be designed to for example overlay an upper lip region and a nasal bridge region of a face. In one form of patient interface a seal-forming portion may comprise an element that surrounds a mouth region in use, e.g. by forming a seal on a lower lip region of a face. In one form of patient interface, a seal-forming portion may comprise a single element that surrounds both nares and a mouth region in use. These different types of patient interfaces may be known by a variety of names by their manufacturer including nasal masks, full-face masks, nasal pillows, nasal puffs and oro-nasal masks.

One type of seal-forming portion extends around the periphery of the patient interface, and is intended to seal against the user's face when force is applied to the patient interface with the seal-forming portion in confronting engagement with the user's face. The seal-forming portion may include an air or fluid filled cushion, or a moulded or formed surface of a resilient seal element made of an elastomer such as a rubber. With this type of seal-forming portion, if the fit is not adequate, there will be gaps between the seal-forming portion and the face, and additional force will be required to force the patient interface against the face in order to achieve a seal.

Another type of seal-forming portion incorporates a flap seal of thin material so positioned about the periphery of the mask so as to provide a self-sealing action against the face of the user when positive pressure is applied within the mask. Like the previous style of seal forming portion, if the match between the face and the mask is not good, additional force may be required to effect a seal, or the mask may leak. Furthermore, if the shape of the seal-forming portion does not match that of the patient, it may crease or buckle in use, giving rise to leaks.

Another type of seal-forming portion may comprise a friction-fit element, e.g. for insertion into a naris.

Another form of seal-forming portion may use adhesive to effect a seal. Some patients may find it inconvenient to constantly apply and remove an adhesive to their face.

A range of patient interface seal-forming portion technologies are disclosed in the following patent applications, assigned to ResMed Limited: WO 1998/004,310; WO 20061074,513; WO 2010/135.785.

2.2.4.2 Positioning and Stabilising

A seal-forming portion of a patient interface used for positive air pressure therapy is subject to the corresponding force of the air pressure to disrupt a seal. Thus a variety of techniques have been used to position the seal-forming portion, and to maintain it in sealing relation with the appropriate portion of the face.

One technique is the use of adhesives. See for example US Patent publication US 2010/0000534.

Another technique is the use of one or more straps and stabilising harnesses. Many such harnesses suffer from being one or more of ill-fitting, bulky, uncomfortable and awkward to use.

Document WO 2013/026092 A1, which is hereby incorporated by reference in its entirety, discloses a headgear, mask and accessory components. FIG. 4b shows a perspective view of the headgear 100 and FIG. 4c shows a plan view of the headgear 100 according to WO 2013/026092. The headgear 100 includes two lateral crown sections or straps 102, 104 and an upper crown section or strap 106 forming a ring-like shape or crown strap assembly configured to fit the crown of a patient's head. Upper mask connection straps 108 and lower mask connection straps 110 are adapted to hold a mask in place on a patient's face. The upper and lower mask connection straps 108, 110 are connected to the upper crown strap 106 and/or the lateral crown straps 102, 104 by ultrasonic welding (shaded areas in the respective connection portions as shown in FIG. 4c). The lower straps 110 are connected such that a joint 115 interconnects the lower straps 110. The joint 115 also interconnects the end portions 102a, 104a of the lateral crown straps 102, 104 and the lower straps 110. In other words, the lateral crown straps 102, 104 both comprise at their lower ends free end portions 102a, 104a forming the neck part of a ring-like crown covering assembly. The end portions 102a. 104a are connected by a joint 115 (see FIGS. 4b and 4c). The joint 115 is substantially parallel to the sagittal or median plane of a user.

Moreover the headgear of the mask Mirage FX™ sold by ResMed Limited comprises a crown section made of one piece of material and being cut out from one material sheet which is then looped and stitched together at the same position as the joint of WO 2013/026092 in order to form a ring-like crown covering assembly.

A joint located in the sagittal or median plane of the user may cause discomfort in the nape of the neck, particularly if the end portions of the lateral crown sections are stitched together. Moreover, these joints require a certain minimum width in order to securely join the two end portions of the lateral crown sections. Such an increased width increases the overall footprint of the headgear. Headgears for PAP therapy are generally used during the night for extended periods. The footprint is critical for overall sleeping comfort since an increased footprint leads to a reduced air circulation at portions covered by the headgear and the user might sweat in covered areas. The increased footprint additionally leads to an increased usage of headgear material thereby increasing material costs of a headgear. Moreover, headgears with an increased footprint may be considered more intrusive, which generally decreases the users' willingness to wear such "medical devices". The manufacturing of the stitch is complex and requires increased material wastage. The whole headgear of the prior art masks are often manufactured of the same material which limits design variation and costs savings by using different (cheaper) materials.

Presently available prior art headgears with lateral crown sections being connected at its end portions are limited concerning a further optimization of the distribution of the mask holding forces around the users' head and/or of the adaption of the headband's general overall shape to the head shape of the average user.

2.2.4.3 Vent Technologies

Some forms of patient interface systems may include a vent to allow the washout of exhaled carbon dioxide. Many such vents are noisy. Others may block in use and provide insufficient washout. Some vents may be disruptive of the sleep of a bed-partner 1100 of the patient 1000, e.g. through noise or focussed airflow.

ResMed Limited has developed a number of improved mask vent technologies. See WO 1998/034,665; WO 2000/078,381; U.S. Pat. No. 6,581,594; US Patent Application; US 2009/0050156: US Patent Application 2009/0044808.

Table of noise of prior masks (ISO 17510-2: 2007, 10 cmH$_2$O pressure at 1 m)

| Mask name | Mask type | A-weighted sound power level dB(A) (uncertainty) | A-weighted sound pressure dB(A) (uncertainty) | Year (approx.) |
|---|---|---|---|---|
| Glue-on (*) | nasal | 50.9 | 42.9 | 1981 |
| ResCare standard (*) | nasal | 31.5 | 23.5 | 1993 |
| ResMed Mirage (*) | nasal | 29.5 | 21.5 | 1998 |
| ResMed UltraMirage | nasal | 36 (3) | 28 (3) | 2000 |
| ResMed Mirage Activa | nasal | 32 (3) | 24 (3) | 2002 |
| ResMed Mirage Micro | nasal | 30 (3) | 22 (3) | 2008 |
| ResMed Mirage SoftGel | nasal | 29 (3) | 22 (3) | 2008 |
| ResMed Mirage FX | nasal | 26 (3) | 18 (3) | 2010 |
| ResMed Mirage Swift (*) | nasal pillows | 37 | 29 | 2004 |
| ResMed Mirage Swift II | nasal pillows | 28 (3) | 20 (3) | 2005 |
| ResMed Mirage Swift LT | nasal pillows | 25 (3) | 17 (3) | 2008 |

((*) one specimen only, measured using test method specified in ISO3744 in CPAP mode at 10 cmH$_2$O)

Sound Pressure Values of a Variety of Objects are Listed Below

| Object | A-weighted sound pressure dB(A) | Notes |
|---|---|---|
| Vacuum cleaner: Nilfisk Walter Broadly Litter Hog: B+ Grade | 68 | ISO3744 at 1 m distance |
| Conversational speech | 60 | 1 m distance |
| Average home | 50 | |
| Quiet library | 40 | |
| Quiet bedroom at night | 30 | |
| Background in TV studio | 20 | |

2.2.4.4 Nasal Pillow Technologies

One form of nasal pillow is found in the Adam Circuit manufactured by Puritan Bennett. Another nasal pillow, or nasal puff is the subject of U.S. Pat. No. 4,782,832 (Trimble et al.), assigned to Puritan-Bennett Corporation.

ResMed Limited has manufactured the following products that incorporate nasal pillows: SWIFT nasal pillows mask. SWIFT II nasal pillows mask, SWIFT LT nasal pillows mask, SWIFT FX nasal pillows mask and LIBERTY full-face mask. The following patent applications, assigned to ResMed Limited, describe nasal pillows masks: International Patent Application WO2004/073,778 (describing amongst other things aspects of ResMed SWIFT nasal pillows), US Patent Application 2009/0044808 (describing amongst other things aspects of ResMed SWIFT LT nasal pillows); International Patent Applications WO 2005/063, 328 and WO 2006/130,903 (describing amongst other things aspects of ResMed LIBERTY full-face mask): International Patent Application WO 2009/052,560 (describing amongst other things aspects of ResMed SWIFT FX nasal pillows).

BRIEF SUMMARY OF THE TECHNOLOGY

The present technology is directed towards providing medical devices used in the diagnosis, amelioration, treatment, or prevention of respiratory disorders having one or more of improved comfort, cost, efficacy, ease of use and manufacturability.

A first aspect of the present technology relates to apparatus used in the diagnosis, amelioration, treatment or prevention of a respiratory disorder.

Another aspect of the present technology relates to methods used in the diagnosis, amelioration, treatment or prevention of a respiratory disorder.

Another aspect of the present technology is directed towards overcoming or ameliorating the aforementioned drawbacks of the prior art and providing an improved and/or alternative and/or additional neck strap, crown strap assembly and/or headgear.

Another aspect of the present technology is directed towards increasing the comfort of a headgear. Another aspect is directed towards reducing the manufacturing costs, and the material costs. Another aspect is to improve the overall appearance of a headgear.

Another aspect of the present technology is directed towards a neck strap for a headgear. In an example, the neck strap comprises first and/or second lower connection portions for connecting first and/or second lower mask connection straps. Additionally, the neck strap may comprise first and/or second upper connection portions for connecting a first and/or second lateral (crown) straps.

In an example of the present technology, headgear will be taken to mean a form of positioning and stabilizing structure designed for use on a patient's head. In an example, the headgear comprises a collection of one or more straps, ties and stiffeners configured to locate and retain a patient interface in position on a patient's face for delivery of respiratory therapy. Some ties may be formed of a soft, flexible, elastic material such as a laminated composite of foam and fabric.

An aspect of the present technology relates to a neck strap for a headgear that eliminates the joint in the sagittal or median plane. Thus no stitch is provided in the plane through the middle of the head. A stitch in that area of the neck may be uncomfortable. Having no joint in that area may also allow the width of the neck strap in that area to be reduced, which may lead to a reduced overall footprint. The material costs may also be reduced. Advantageously, the positioning of the straps may be further improved and the overall shape of the headgear may be better adapted to the average user.

Another aspect of the present technology relates to a neck strap and crown straps for a headgear structured to allow for additional head mobility in use without impacting the back of the patient's neck and the force applied to the patient by the patient interface and seal forming structure. In an example of the present technology, the neck strap includes a smaller overall size and a curvature in an upper edge thereof that allows more head mobility in a posterior direction.

In an example of the present technology, the neck strap may be substantially flat. The neck strap may comprise at least one, e.g., at least two or two opposing major side edge(s) or major side surface(s). In an example, the at least one of the (opposing) major side edge(s) comprise(s) a curved or arc-shaped portion. The curvature of the major side edge may be concave. In an example, the two major side edges are curved. The neck strap may have at least partially a reduced width between opposing major side edges, particularly in the curved portion. The neck strap may comprise at least one, e.g., at least two or two opposing minor side edge(s) or minor side surface(s). The major side edge(s) may interconnect the (opposing) minor edges. A first lower connection portion and/or a first upper connection portion may be located at a first of the two minor side edges. A second lower connection portion and/or a second upper connection portion may be located at a second of the two minor side edges.

In an example, the first lower connection portion may extend substantially parallel. e.g., parallel, to an adjacent (lower connection edge) portion of the respective minor side edge. Additionally or alternatively, the second lower connection portion may extend substantially parallel, e.g., parallel, to an adjacent (lower connection edge) portion of the respective minor side edge. The first upper connection portion may extend substantially parallel, e.g., parallel, to an adjacent (first upper connection edge) portion of the respective minor side edge. Additionally or alternatively, the second upper connection portion may extend substantially parallel, e.g., parallel, to an adjacent (second upper connection edge) portion of the respective minor side edge. The first and/or second upper or lower connection edge portion(s) may be (an) edge portion(s) of the at least one minor side edge, which may be located in the transition of neck strap to the strap(s) fixed to the respective portion of the neck strap.

In an example, the first and/or second lower connection portion may be oriented substantially perpendicular, e.g., perpendicular, to the main axis of extension of the respective first and/or second lower mask connection strap. In an example, the first and/or second (lower connection edge) portion(s) of the minor side edge(s) may be oriented substantially perpendicular, e.g., perpendicular, to the main axis of extension of the respective first and/or second lower mask connection strap. The first and/or second lower mask connection straps and the neck strap may be configured as one piece, e.g., cut out of one material sheet. Such a one piece neck strap may be connected via upper first and/or second connection portion(s) to the at least one lateral crown strap. The costs for welding may be reduced while the material waste may only be moderately increased if at all.

In an example, the first and/or second upper connection portion(s) may be oriented in an acute angle to the main axis of extension of the respective first and second lateral crown strap, which is connectable to the neck strap. In an example, the first and/or second (upper connection edge) portion(s) of the minor side edge(s) may be oriented in an acute angle to the main axis of extension of the respective first and/or second lateral crown strap to be connected to the neck strap. In an example, respective first and/or second transitional edge portion(s) may be connected (substantially) tangentially with the respective first and/or second (upper connection edge) portion(s) of the minor side edge(s). Respective first and/or second transitional edge portion(s) may intersect with respective rust and/or second (lower connection edge) portion(s) of the minor side edge(s) in an angle, e.g., between 60° to 120°, between 75° to 105°, about 90°.

In an example, the neck strap may be symmetrical to a first axis, wherein the first axis in the application position is substantially parallel, e.g., parallel, to the sagittal plane, e.g., to the median plane, of a user. A second axis of the neck strap may extend perpendicular to the first axis. The width perpendicular to the second axis of the neck strap may be lowest in the curved portion of the major side edge(s). The width perpendicular to the second axis may be highest at a cross-section in which a major side edge intersects with a minor side edge. e.g., in which a major side edge intersects with the first or second upper connection edge portion. In an example, at least one major side edge and/or at least one minor side edge may be rounded. In an example, the neck strap may be adapted to be used for a headgear, for instance with upper and lower mask connection straps e.g., holding a breathing mask. The breathing mask may be a nasal mask, a mouth mask or a full face mask, e.g., for a PAP therapy. The neck strap may be adapted for a headgear comprising a three dimensionally formed crown strap assembly.

Another aspect of the present technology relates to a three dimensionally formed crown strap assembly for or of a headgear. The crown strap assembly may comprise at least one, e.g., one, top crown strap, at least two, e.g., two, lateral crown straps and/or a neck strap. The top crown strap and/or the at least two lateral crown straps may be configured as separate elements. The separate elements may be joined together during the manufacturing process. Alternatively, the top crown strap and/or the at least two lateral crown straps may be configured as or made of one piece. In one example, the top crown strap and the at least two lateral crown straps may be cut out of one material sheet. The crown strap assembly may have a generally round three dimensional shape, e.g., that cups the parietal bone and/or occipital bone of the patient's head in use. The crown strap may have a 3D contour curve substantially to fit to the shape of a user's crown back of a user's head. The straps may at least partially not extend in the same plane thereby forming a three-dimensional shape of the crown strap assembly. The top crown strap may be located on the top of the crown in the application position. The top crown strap may extend between a first and second upper mask connection straps. The mask connection straps may extend to the forehead region of the user. In the application position, the neck strap may form the lower part of the ring-like crown strap assembly.

In an example, the lateral crown straps may be located on either side of the crown in the application position. Two lateral crown straps and/or the neck strap may be arranged so as to build a V-shape in a plane view and/or in the application position. The top crown strap and/or at least one of the lateral crown straps may be strap elements having an (substantially) elongated shape. In an example, a "substantially elongated" strap is a strap with slightly arc-shaped sides. A deviation from the rectangular shape in a width direction may be less than twice the width of the strap. In an example, a strap having a significant L-shape or a significantly curved shape may not be considered as a substantially elongated strap. Substantially elongated straps advantageously reduce the material waste. At least two of the lateral crown straps may have (substantially) the same length. At least two of the lateral crown straps may have a mirror-inverted shape. At least one end of the at least one lateral crown strap may have an increased width compared to another portion of the respective strap.

In an example, at least one end, e.g., both ends of at least one lateral crown strap may comprise a front side or front end wall, which extends in an acute angle to the strap's main axis. The acute angle between the front side and the strap's main axis may be (substantially) equal to the acute angle of the first or second upper connection portion and/or the adjacent (upper connection edge) portion of the minor side edge to the strap's main axis. The main axis of at least one lateral crown strap may (substantially) extend straight. In an example, the main axis of the at least one top crown strap (substantially) extends as a curved line. The front side of at least one end of at least one lateral crown strap and/or of the top crown strap may comprise at least one stepped portion. The crown strap assembly may be adapted for a headgear, for instance with upper and lower mask connection straps, e.g., adapted for holding a breathing mask. The breathing mask may be a nasal mask, mouth mask or a full face mask. e.g., for a PAP therapy.

Another aspect of the present technology relates to a headgear including the above crown strap assembly and/or upper and/or lower mask connection straps. The top crown strap and at least one lateral crown strap may be connected at and/or via portions of the upper mask connection straps. Such joints may be constructed as a thinned region to encourage bending. The thinned region may function as a flex point or hinge (e.g., a living hinge) to provide increased flexibility where desired. The flex point or hinge may be reinforced using hot-melt seam tape, or a thinner fabric layer with an adhesive backing, or other reinforcement methods. Such a hinge feature of the connection may permit the headgear to better accommodate the shape of a patient's head. A combination of linear and nonlinear joints may be utilized to achieve a desired level of flexibility and direction of flexion, as well as a desired level of three dimensional shaping to a component made up of a series of parts which were originally a flat material (such as fabric or paper, for example). Such shaping may include darts, tucks, gathers, or a curved seam. An example joint is depicted in FIG. 3-2 of WO2013/026092 A1 which is hereby incorporated by reference.

In an example, the first and second lower mask connection straps may be connected to the neck strap. In an example, the headgear comprises adjustment or fastening members, e.g., with a hook material and a loop material.

In an example, at least two straps selected from the group of mask connection straps, top crown strap lateral crown straps, and/or neck strap may be made of a different material. In an example, at least one of the mask connection straps is made of a different material compared to the top crown strap and/or the two lateral crown straps. The neck strap may be made of a different material compared to the top crown strap, the at least one lateral crown strap(s) and/or at least one upper and/or lower mask connection strap. At least one strap selected from the group of mask connection straps, top crown strap, lateral crown straps, and/or neck strap may at least partially be made of or comprise nylon and/or lycra. At least a portion of the top crown strap, the lateral crown straps and/or the neck strap may comprise different layers, e.g., of different materials. Different layers may be welded one to another. In an example, the strap may comprise different layers of different materials, e.g. an outer layer of an aesthetically pleasing material and/or an inner layer facing the patients head in an application position made of a soft and/or pleasing material. For example, the straps forming the crown assembly may be made of an inexpensive and/or comfortable material. In an example, different materials for different layers of a strap portion and/or different straps may be selected depending on the specific properties/functions/requirements. In an example, the headgear may be BPA-free and Gelamid® may be applied at least for portions of the strap. All above straps may be cut of a sheet material by ultrasonic cutting.

In an example, a strap may be a single layer component such as a textile or fabric, or a composite or multiple layer components such as fabric and foam composites, or outer fabric layers and inner spacer fabrics. The straps may be made of a spandex or elastane/foam composite, or may be formed of other suitable materials (such as a 3D spacer fabric or a double-knit interlock fabric). These straps may be cut from a sheet of material (e.g., flame laminated), or cut from a roll of narrow fabric strap and then thermoformed and ultrasonically welded to create rounded edges before being ultrasonically welded together. The straps may have a geometry that allows them to be nested on the sheet to increase yield, e.g., the geometry may be substantially linear.

In some examples, tape may be overlaid with a thin fabric layer having a thickness of about 0.1 mm and about 1 mm to maintain a desirable soft surface finish. Such thermoplastic sheets may be made from, for example: polyurethane (TPU), polyester, polyamide, polyolefin and aliphatic urethanes. These materials may be customized to provide the optimum performance characteristics for specific applications, and may be produced in a range of colors, opacities, and surface finishes desired for the end use of patient interface equipment for the treatment of sleep disordered breathing, such as in headgear or a mask arrangement. Materials having differing degrees of flexibility may be combined in an alternating manner to form a controlled flex region. Components may be stacked one on top of the other and ultrasonically welded together in a manner that leaves no space therebetween. The patient interface component may be constructed of a soft material, e.g., a soft fabric.

In an example, the thickness of the top crown strap and/or lateral crown straps may be at least partially about 3.8 mm (+−0.5 mm). In an example, the thickness of the neck strap may be at least partially about 4.2 mm (+−0.5 mm). In an example, the thickness of the mask connection straps may be at least partially about 2.5 mm (+−0.5 mm).

In an example, at least two straps selected from the group of mask connection straps, top crown strap, lateral crown straps, and/or neck strap may be connected by welding, e.g., by ultrasonic welding. Exemplary welding is explained in detail in the summary of technology in the publication WO2013/026092 A1 which is incorporated by reference. In particular, FIG. 3-1 and FIG. 3-2 of WO2013/026092 A1 depict an example of the welding of the top crown strap and/or lateral crown straps. Portions of the top crown strap and the upper mask connection straps may overlap and portions of the lateral crown straps and upper mask connection straps also may overlap. These members may be placed in an ultrasonic welding tool, e.g., such as that disclosed in WO2013/026092. An advantage of the ultrasonic welding process is that a flush or butt joint does not increase the thickness of the components at the joint and is visually appealing, unlike stitching where components must be overlapped and which results in an uneven thickness. Even if the edges of the two or more components are butted together and stitched without any or substantial overlapping, the stitches will create a rougher, stiffened and raised joint. Further, the ultrasonic flush or butt joint may result in a smooth connection that may reduce skin irritation, chaffing or facial marking, even when reinforced with seam reinforcement tape. An advantage of using an overlapped ultrasonic weld variation is that multiple components may be joined in a single machine in one operation. Furthermore, the ultrasonic welding process may be designed such that the joint is embodied as a thinned region or thinned portion between the components.

In an example, the width of the top crown strap and/or lateral crown straps may, at least partially, be reduced compared to the width of at least one of the mask connection straps. Accordingly, the footprint may be further reduced and the material usage may be reduced, too. The width of the top, lateral or neck strap(s) and thus the footprint may be (additionally) reduced by using different materials, different strap thicknesses and/or different compositions. Different materials and/or cheaper materials may be used for some parts or portions of a headgear, e.g., with the same seal support efficacy and/or comfort. The neck strap may have an increased thickness compared to at least one lower mask connection strap. This may increase the comfort.

Another aspect of the present technology relates to a neck strap for a headgear including first and second lower connection portions for connecting first and second lower mask connection straps, and first and second upper connection portions for connecting a first and second lateral crown straps. The neck strap may be substantially flat. The neck strap may comprise two opposing major side edges. The at least one of the opposing major side edges may comprise a curved portion. The curvature of the major side edge may be concave. The two major side edges may be curved and the neck strap may have at least partially a reduced width between opposing major side edges in the curved portion. The neck strap may comprise two opposing minor side edges wherein the major side edges interconnect the opposing minor edges. The first lower connection portion and/or the first upper connection portion may be located at a first of the two minor side edges, and/or the second lower connection portion and/or the second upper connection portion may be located at a second of the two minor side edges. The first and/or second lower connection portion may extend substantially parallel to an adjacent portion of the respective minor side edge, and/or the first and/or second upper connection portion may extend substantially parallel to an adjacent portion of the respective minor side edge. The first and/or second lower connection portion and/or respective portions of the minor side edges may be oriented substantially perpendicular to the main axis of extension of the respective first and/or second lower mask connection strap. The first and second upper connection portions and/or the adjacent portions of the minor side edges may be oriented in an acute angle to the main axis of extension of the respective first and second lateral crown strap. Respective first and second transitional edge portions may be connected tangentially with the respective portions of the minor side edges adjacent to the respective first and second upper connection portions. Respective first and second transitional edge portions may intersect with the respective portions of the minor side edges adjacent to the respective first and second lower connection portions in an angle. e.g., between 60° to 120°, between 75° to 105°, about 90°. The neck strap may be symmetrical to a first axis, wherein the first axis in the application position may be substantially parallel to the sagittal plane of a user. A second axis of the neck strap may extend perpendicular to the first axis. The width perpendicular to the second axis of the neck strap may be lowest in the curved portion of the major side edges. The width perpendicular of the second axis of the neck strap may be highest at a cross-section in which a major side edge intersects with a minor side edge. e.g., intersects with the respective portion of the minor side edge adjacent to the respective first and second upper connection portion. The major side edges and/or the minor side edges may be rounded. The neck strap may be adapted for a headgear with upper and lower mask connection straps adapted for holding a breathing mask. The breathing mask may be a nasal mask, a mouth mask or a full face mask, e.g., for a PAP therapy. The neck strap may be adapted for a headgear comprising a three dimensionally formed crown strap assembly.

Another aspect of the present technology relates to a three dimensionally formed crown strap assembly for a headgear comprising a top crown strap, two lateral crown straps, and a neck strap in accordance with an example of the present technology. The top crown strap and the lateral crown straps may be configured as separate elements. The crown strap assembly may have a generally round three-dimensional shape that cups the parietal bone and occipital bone of the patient's head in use. The top crown strap may extend between a first and second upper mask connection straps, and the mask connections straps may extend to the forehead region of the user. The two lateral crown straps and the neck strap may be arranged so as to build a V-shape in a plane view. The top crown strap and/or at least one of the lateral crown straps may be separate strap elements having a substantially elongated shape. The lateral crown straps may have substantially the same length. The lateral crown straps may have a mirror-inverted shape. At least one end of at least one lateral crown strap may have an increased width compared to another portion of the respective strap. At least one end. e.g., both ends, of at least one lateral crown strap may comprise a front side, which extends in an acute angle to the strap's main axis. The acute angle between the front side and the strap's main axis may be substantially equal to the acute angle of the first and/or second upper connection portion and/or the adjacent portion of the minor side edge to the strap's main axis. The main axis of at least one lateral crown strap may substantially extend straight. The main axis of the top crown strap may substantially extend as a curved line. The front side of at least one end of the lateral crown strap and/or of the top crown strap may comprise a stepped portion. The crown strap assembly may be adapted for a headgear with upper and lower mask connection straps adapted for holding a breathing mask. The breathing mask may be a nasal mask, mouth mask or a full face mask, e.g., for a PAP therapy.

Another aspect of the present technology relates to headgear comprising the crown strap assembly in accordance with an example of the present technology and upper mask connection straps. The top crown strap and at least one lateral crown strap may be connected at and/or via portions of the upper mask connection straps. The headgear may further comprise first and second lower mask connection straps connected to the neck strap. The headgear may comprise adjustment or fastening members. At least two straps may be selected from the group of mask connection straps, top crown strap, lateral crown straps, and/or neck strap may be made of a different material. At least one of the mask connection straps may be made of a different material compared to the top crown strap and/or the two lateral crown straps.

In an example, the neck strap may be made of a different material compared to the top crown strap and/or the lateral crown straps. At least one strap may be selected from the group of mask connection straps, top crown strap, lateral crown straps, and/or neck strap may be made of nylon or lycra. At least a portion of the top crown strap, the lateral crown straps and/or the neck strap may comprise different layers of different materials, e.g., welded one to another. The thickness of the top crown strap and/or the lateral crown straps may be at least partially about 3.8 mm (+−0.5 mm), and/or the thickness of the neck strap may be at least partially about 4.2 mm (+−0.5 mm), and/or the thickness of the mask connection straps may be at least partially about 2.5 mm (+−0.5 mm). At least two straps selected from the group of mask connection straps, top crown strap, lateral crown straps, and/or neck strap may be connected by welding. The width of the top crown strap and/or lateral crown straps may be at least partially reduced compared to the width of at least one of the mask connection straps.

Another aspect of the present technology relates to a patient interface for sealed delivery of a flow of breathable gas at a continuously positive pressure with respect to ambient air pressure to an entrance to the patient's airways including at least entrance of a patient's nares, wherein the patient interface is configured to maintain a therapy pressure in a range of about 4 cmH2O to about 30 cmH2O above ambient air pressure in use, throughout the patient's respiratory cycle, while the patient is sleeping, to ameliorate sleep disordered breathing. The patient interface includes a scaling-forming structure adapted to form a seal against the patient's airways, a positioning and stabilising structure to maintain the seal-forming structure in sealing contact with an area surrounding an entrance to the patient's airways while maintaining a therapeutic pressure at the entrance to the patient's airways, a plenum chamber pressurised at a pressure above ambient pressure in use, and a gas washout vent configured to allow a flow of patient exhaled CO2 to an exterior of the patient interface to minimise rebreathing of exhaled CO2 by the patient. The positioning and stabilising structure includes a headgear including a crown strap assembly, first and second upper connection straps provided to the crown strap assembly and adapted to connect to respective upper headgear connectors of the patient interface, and first and second lower connection straps provided to the crown strap assembly and adapted to connect to respective lower headgear connectors of the patient interface. The crown strap assembly includes a neck strap, first and second lateral crown straps and a top crown strap adapted to cup the parietal bone and the occipital bone of the patient's head. The neck strap includes a one-piece man body including first and second lower connection portions to connect to respective first and second lower connection straps and first and second upper connection portions to connect to respective first and second lateral crown straps.

An aspect of one form of the present technology is a method of manufacturing apparatus.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

4. BRIEF DESCRIPTION OF THE SEVERAL VIEWS OF THE DRAWINGS

The present technology is illustrated by way of example, and not by way of limitation, in the figures of the accompanying drawings, in which like reference numerals refer to similar elements including:

4.1 Treatment Systems

FIG. 1a shows a system in accordance with the present technology. A patient 1000 wearing a patient interface 3000, receives a supply of air at positive pressure from a PAP device 4000. Air from the PAP device is humidified in a humidifier 5000, and passes along an air circuit 4170 to the patient 1000.

4.2 Therapy 4.2.1 Respiratory System

Figure 2A:
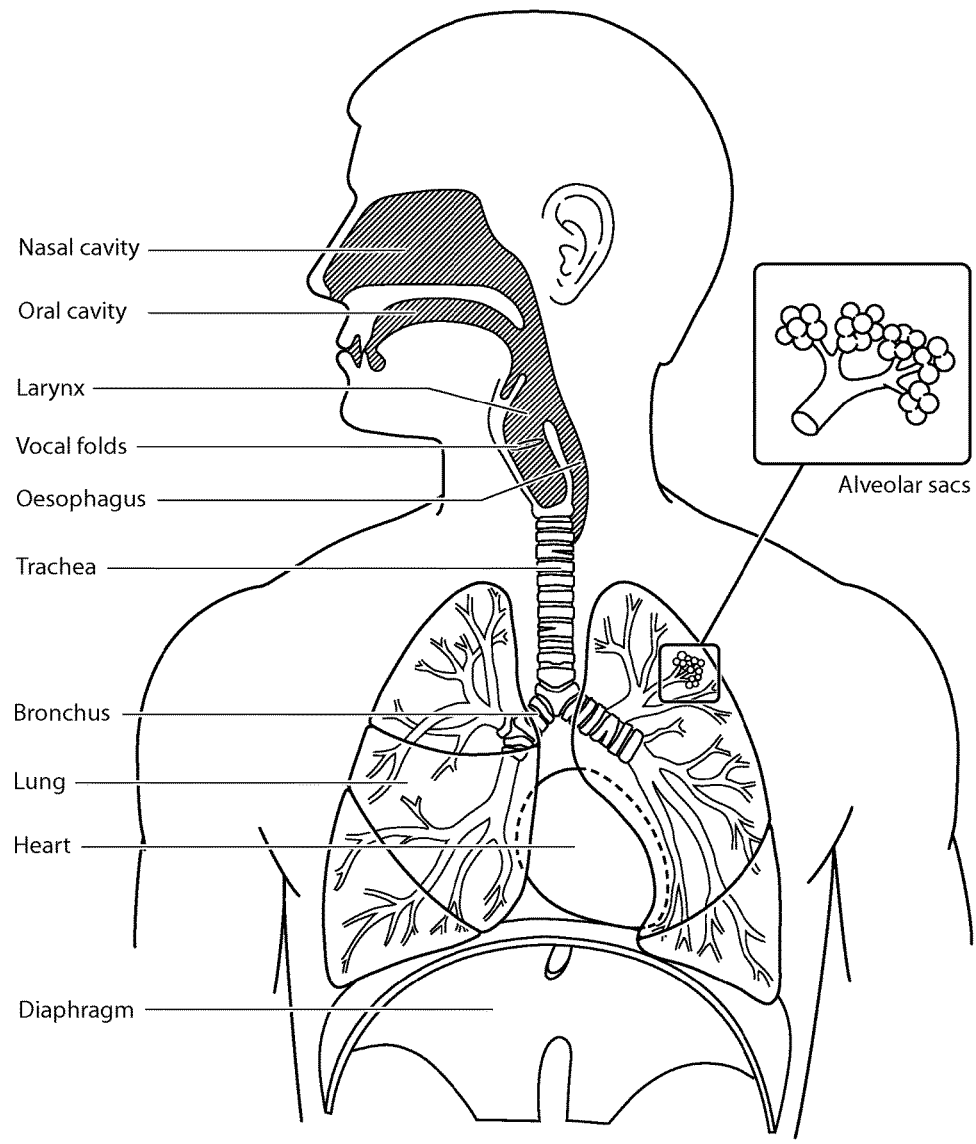

FIG. 2a shows an overview of a human respiratory system including the nasal and oral cavities, the larynx, vocal folds, oesophagus, trachea, bronchus, lung, alveolar sacs, heart and diaphragm.

Figure 2B:
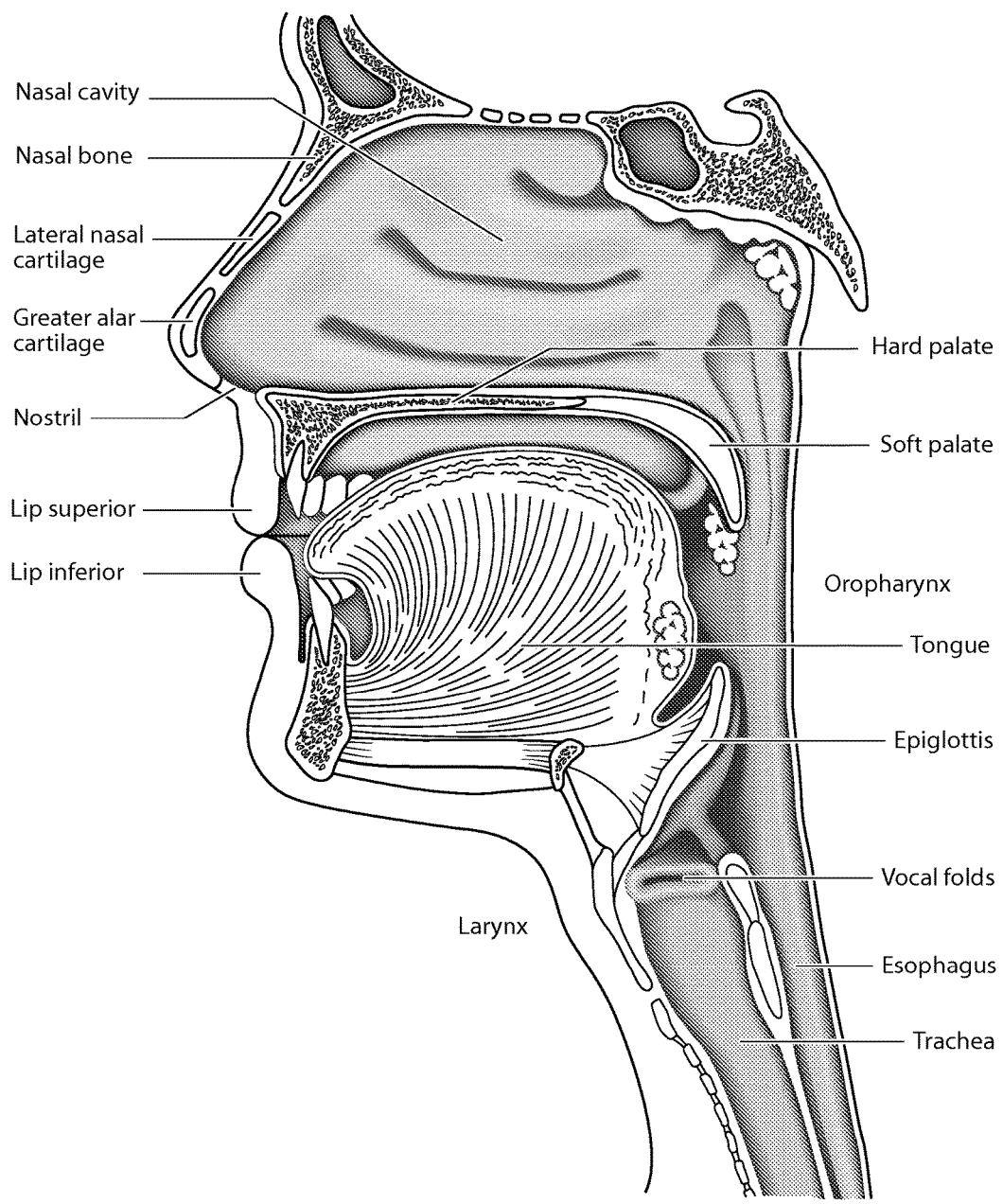

FIG. 2b shows a view of a human upper airway including the nasal cavity, nasal bone, lateral nasal cartilage, greater alar cartilage, nostril, lip superior, lip inferior, larynx, hard palate, soft palate, oropharynx, tongue, epiglottis, vocal folds, oesophagus and trachea.

4.2.2 Facial Anatomy

Figure 2C:
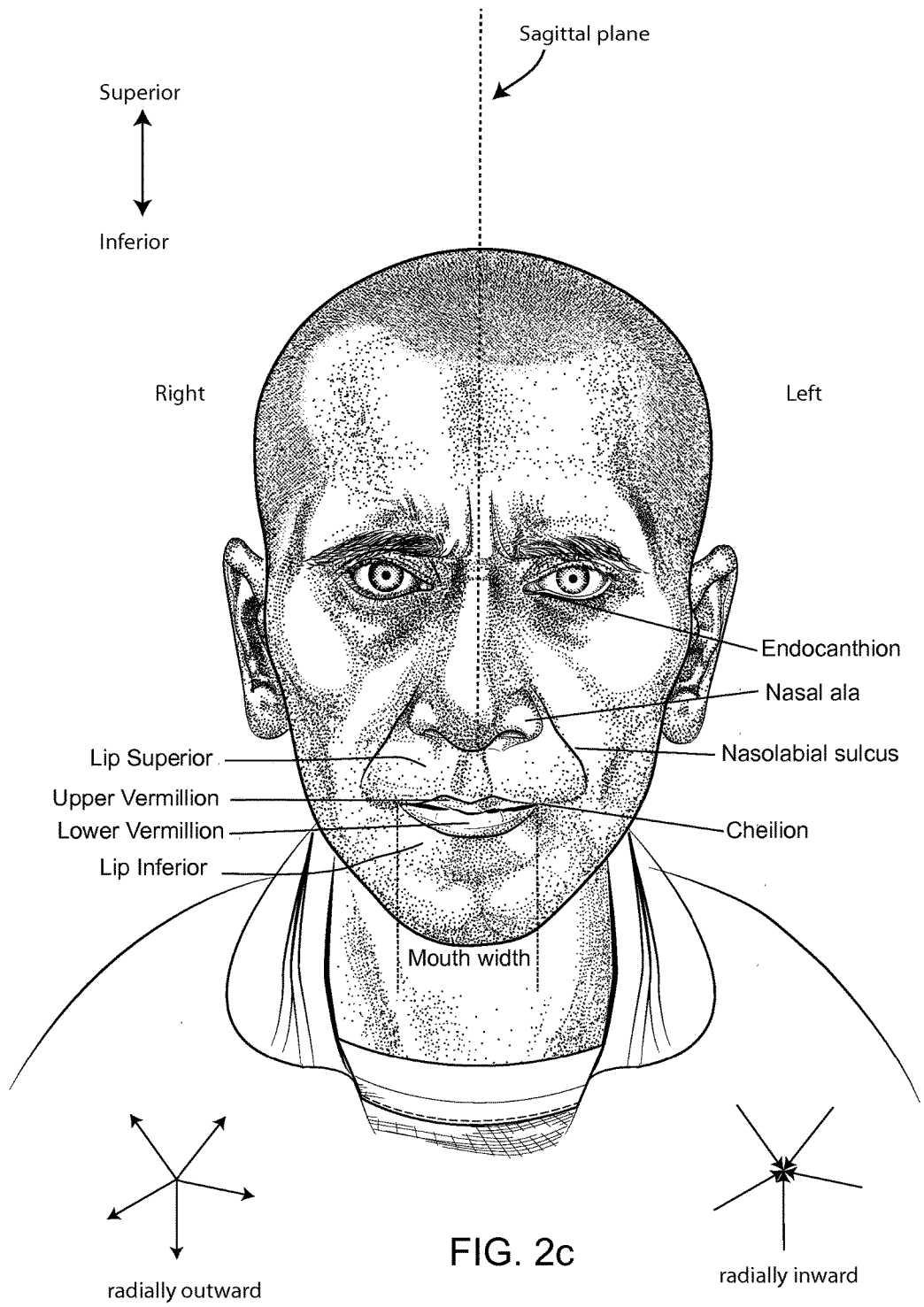

FIG. 2c is a front view of a face with several features of surface anatomy identified including the lip superior, upper vermillion, lower vermillion, lip inferior, mouth width, endocanthion, a nasal ala, nasolabial sulcus and cheilion.

Figure 2D:
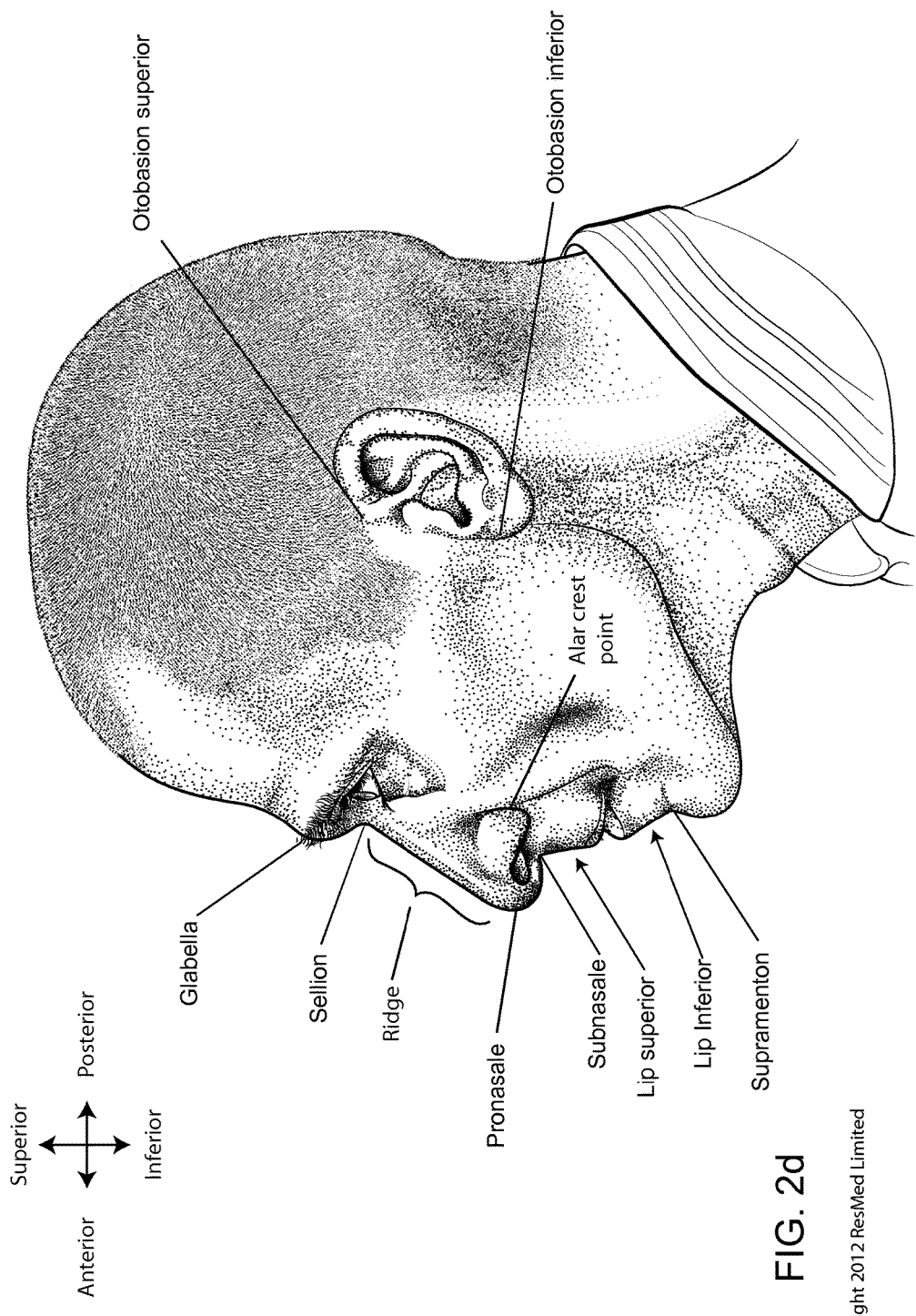

FIG. 2d is a side view of a head with several features of surface anatomy identified including glabella, sellion, pronasale, subnasale, lip superior, lip inferior, supramenton, nasal ridge, otobasion superior and otobasion inferior. Also indicated are the directions superior & inferior, and anterior & posterior.

Figure 2E:
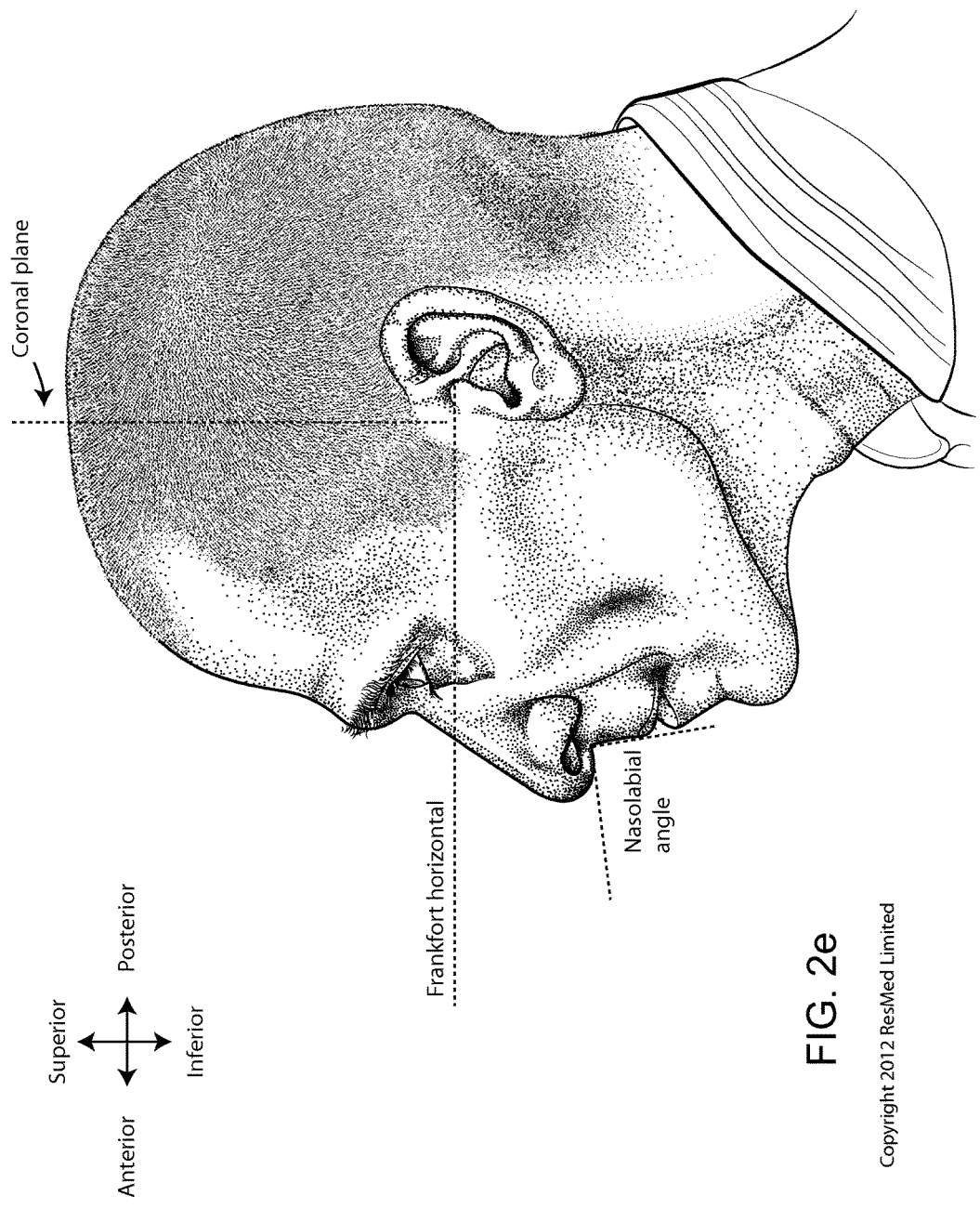

FIG. 2e is a further side view of a head. The approximate locations of the Frankfort horizontal and nasolabial angle are indicated.

Figure 2F:
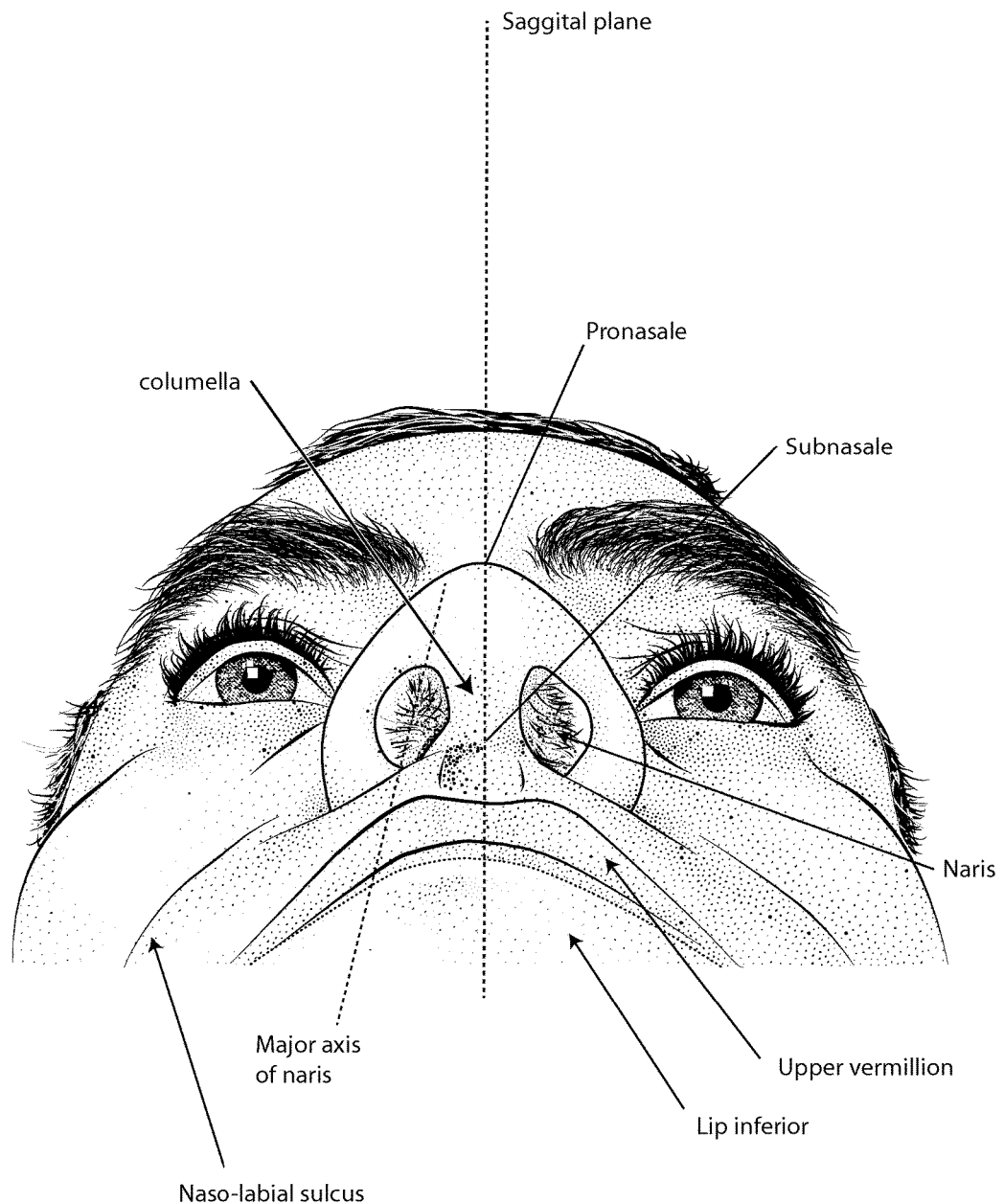

FIG. 2f shows a base view of a nose.

Figure 2I:
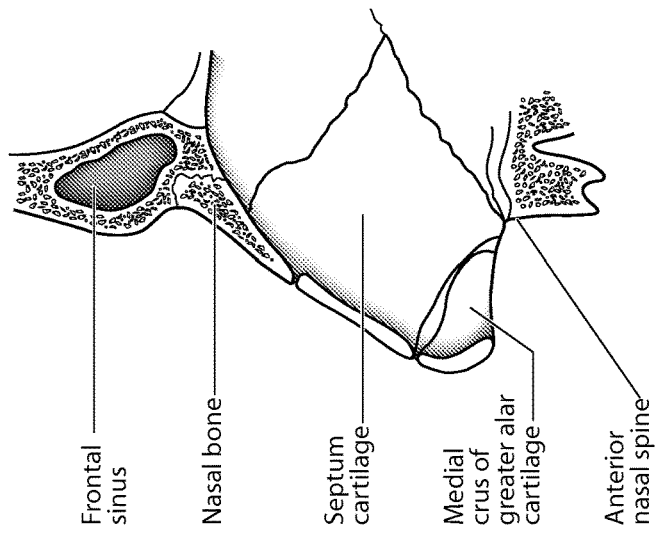
Figure 2H:
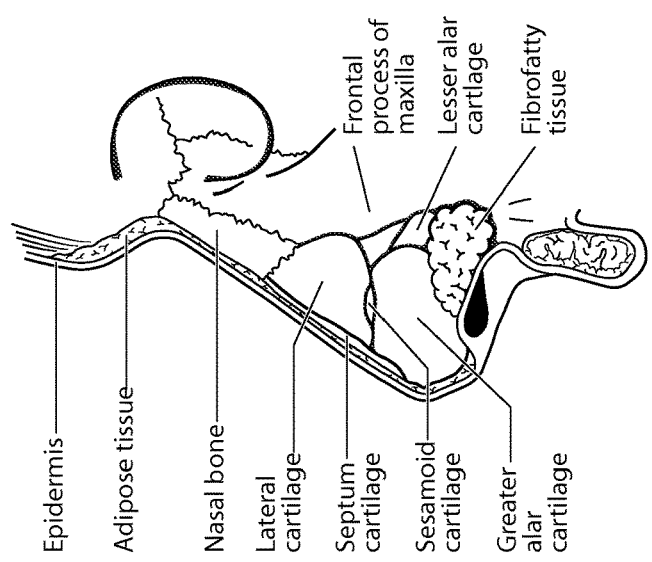
Figure 2G:

FIG. 2g shows a side view of the superficial features of a nose.

FIG. 2h shows subcutaneal structures of the nose, including lateral cartilage, septum cartilage, greater alar cartilage, lesser alar cartilage and fibrofatty tissue.

FIG. 2i shows a medial dissection of a nose, approximately several millimeters from a sagittal plane, amongst other things showing the septum cartilage and medial crus of greater alar cartilage.

Figure 2J:
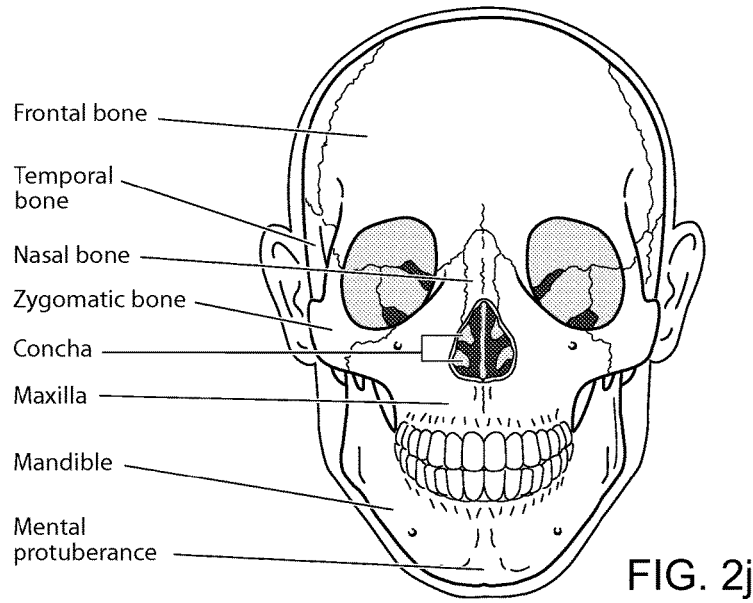

FIG. 2j shows a front view of the bones of a skull including the frontal, temporal, nasal and zygomatic bones. Nasal concha are indicated, as are the maxilla, mandible and mental protuberance.

Figure 2K:
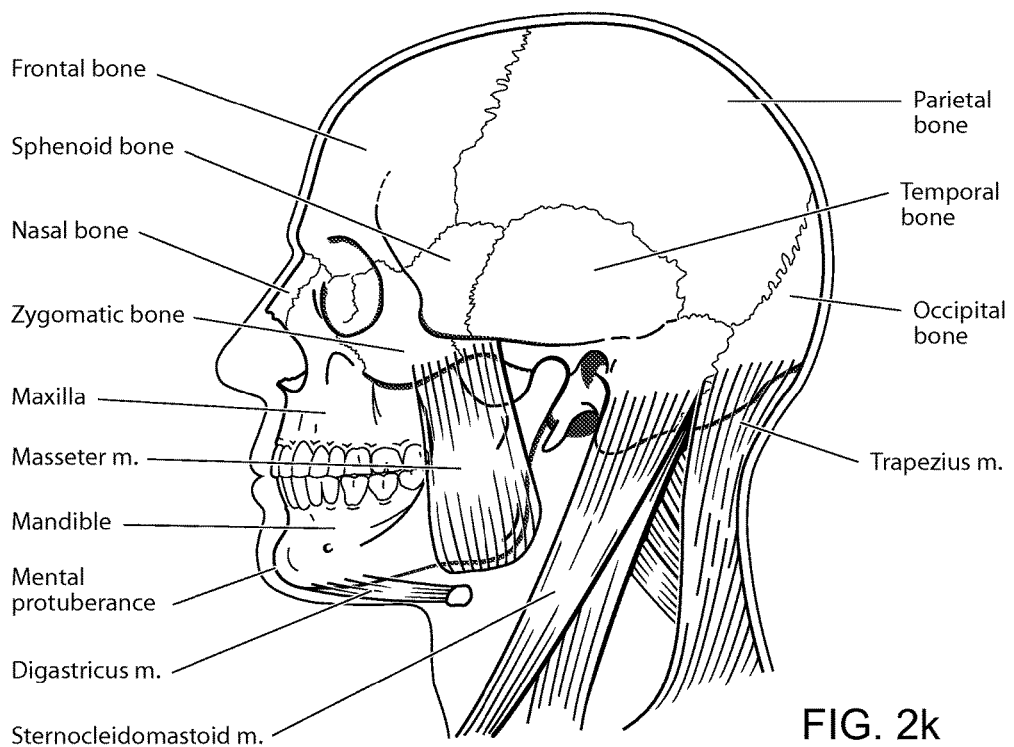
Figure 2I:
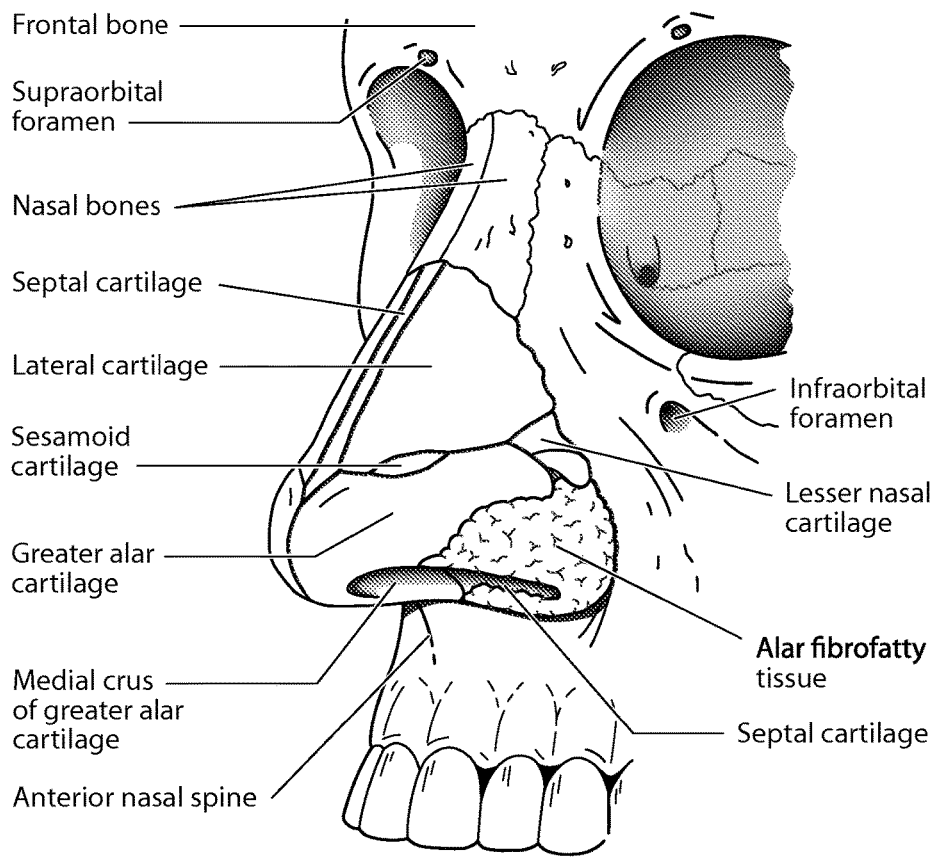

FIG. 2k shows a lateral view of a skull with the outline of the surface of a head, as well as several muscles. The following bones are shown: frontal, sphenoid, nasal, zygomatic, maxilla, mandible, parietal, temporal and occipital. The mental protuberance is indicated. The following muscles are shown: digastricus, masseter sternocleidomastoid and trapezius.

FIG. 2l shows an anterolateral view of a nose.

4.3 Pap Device and Humidifier

Figure 3A:
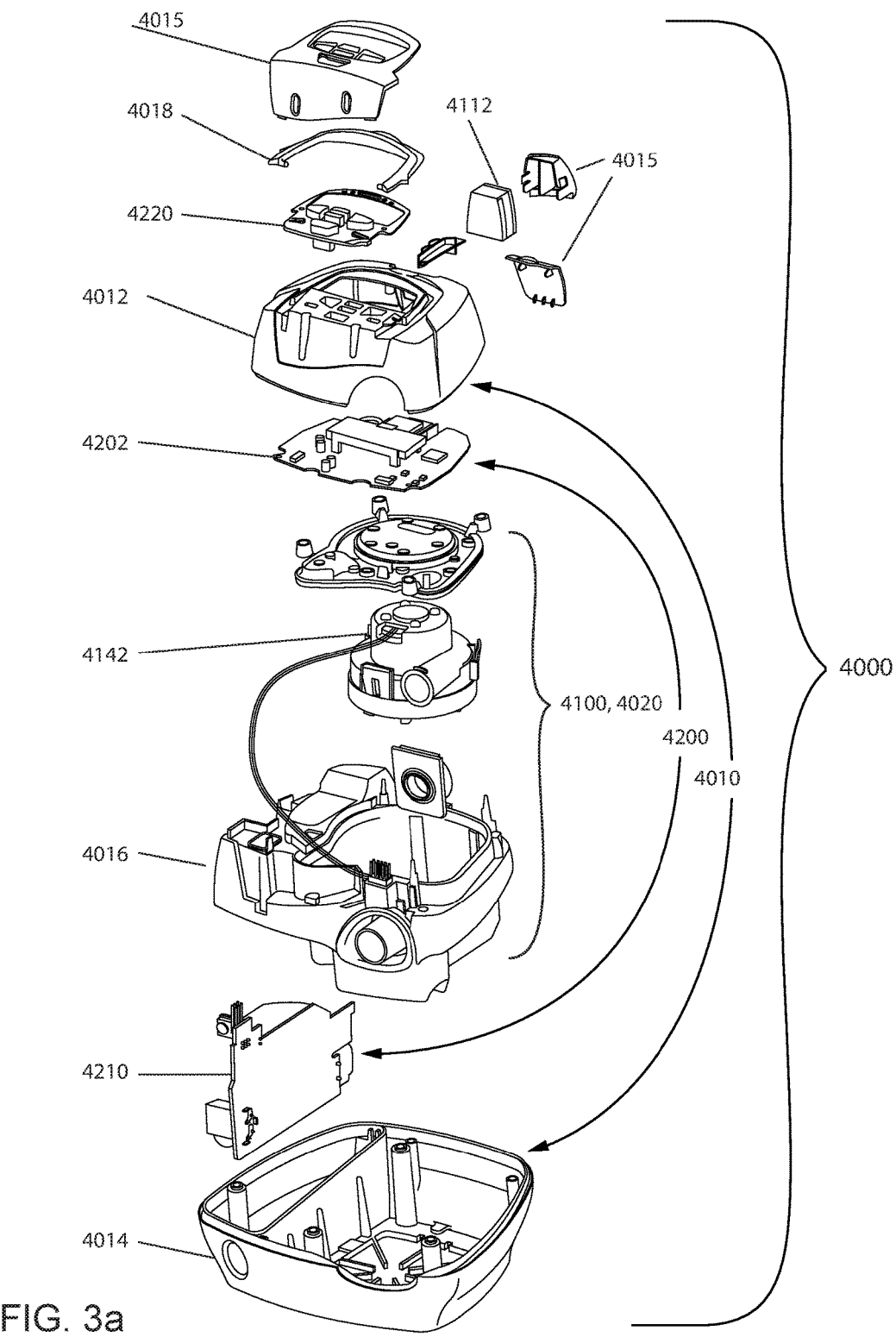

FIG. 3a shows a PAP device in accordance with one form of the present technology.

Figure 3B:
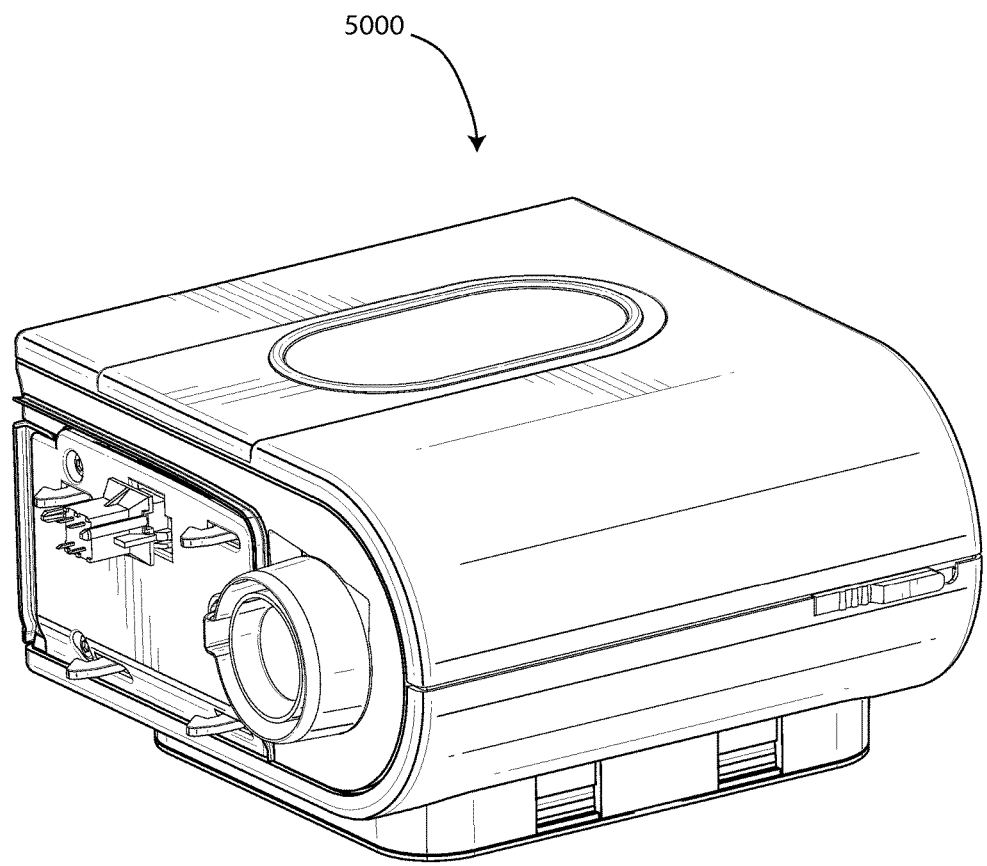

FIG. 3b shows a humidifier in accordance with one aspect of the present technology.

Figure 3C:
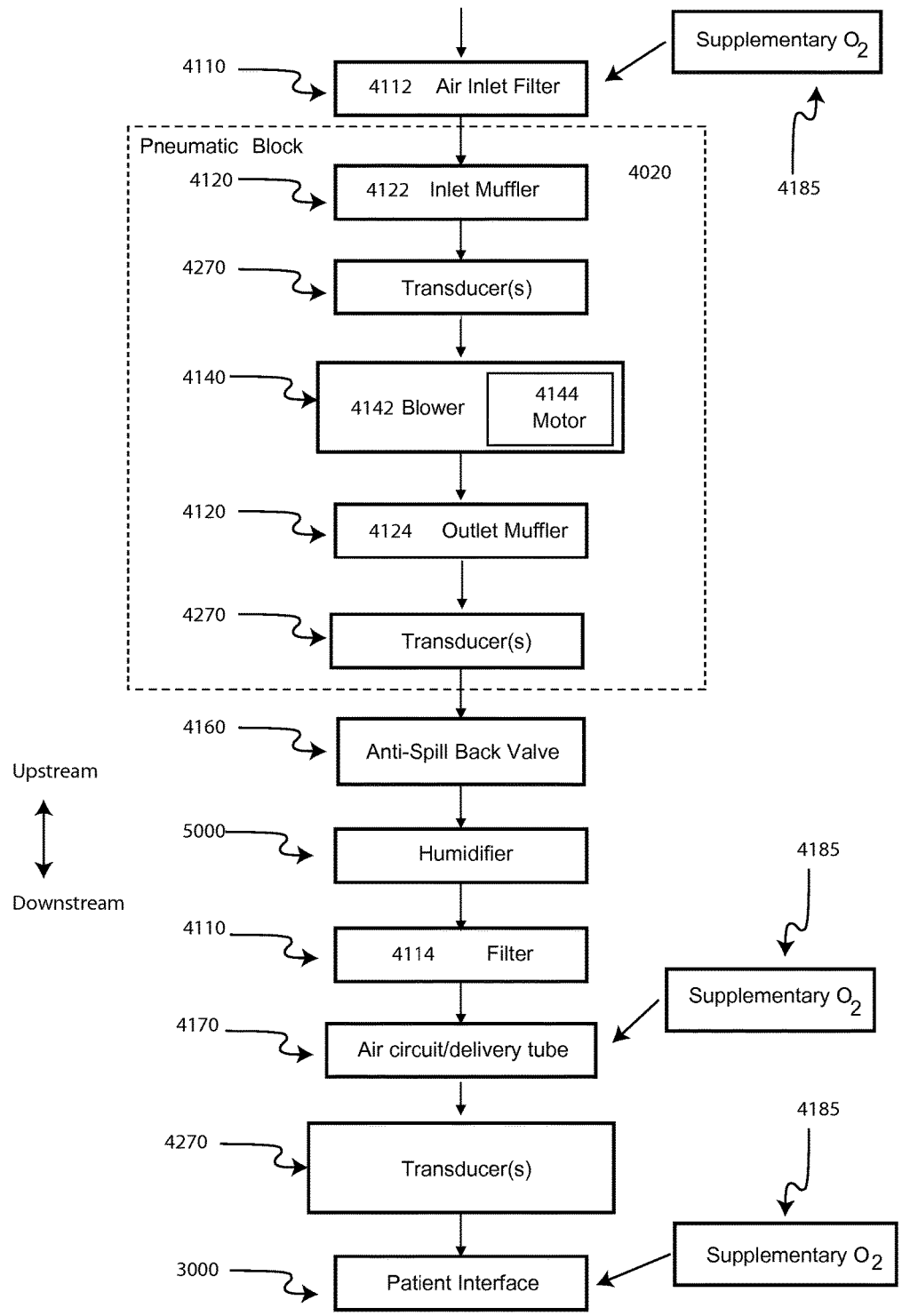

FIG. 3c shows a schematic diagram of the pneumatic circuit of a PAP device in accordance with one form of the present technology. The directions of upstream and downstream are indicated.

4.4 Patient Interface

FIG. 4a is a perspective view of a patient interface in accordance with one form of the present technology.

FIGS. 4b and 4c show a headgear having lateral crown straps with prior art end portions.

Figure 5:
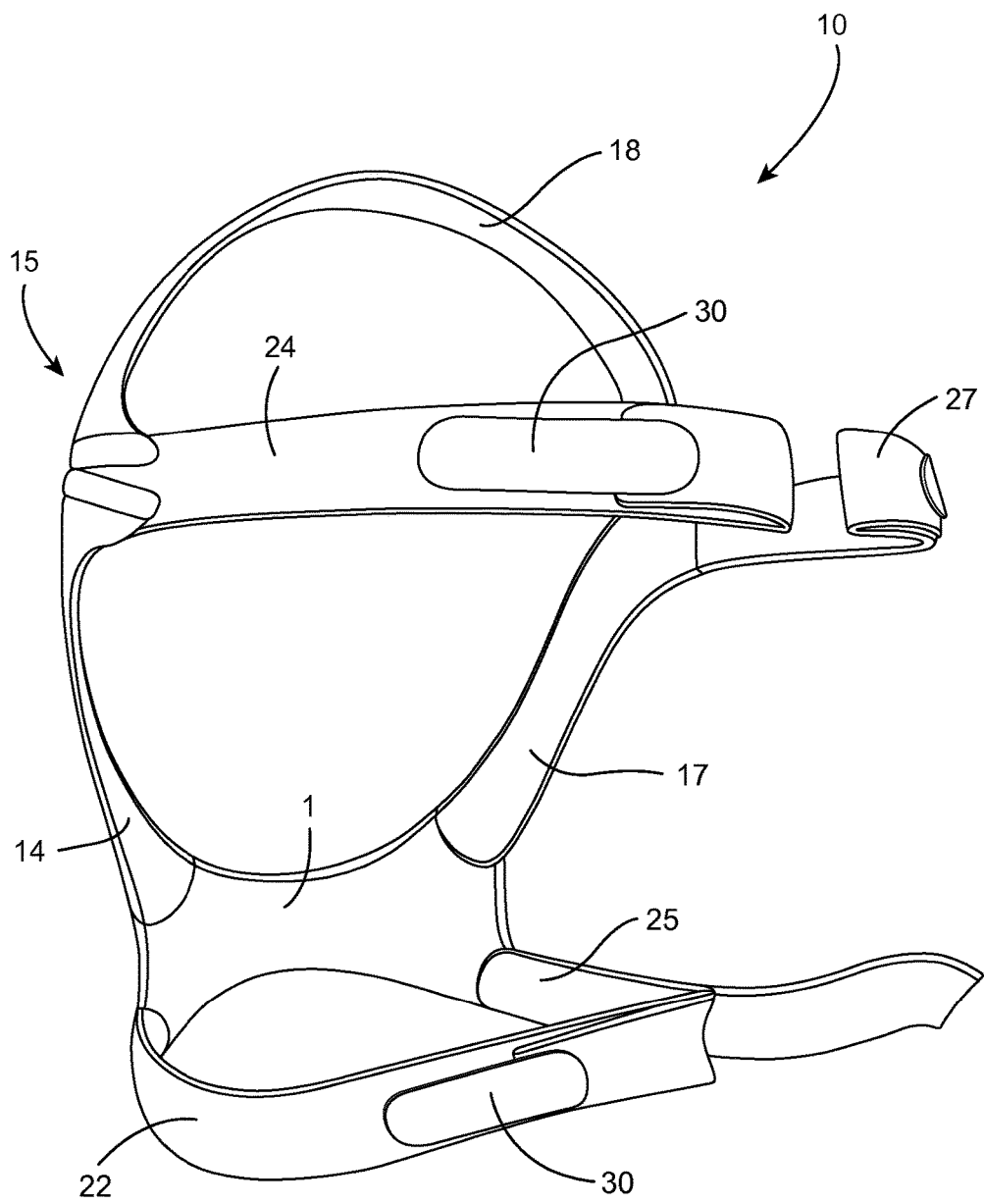

FIG. 5 is a front perspective view of headgear according to an example of the present technology.

Figure 6:
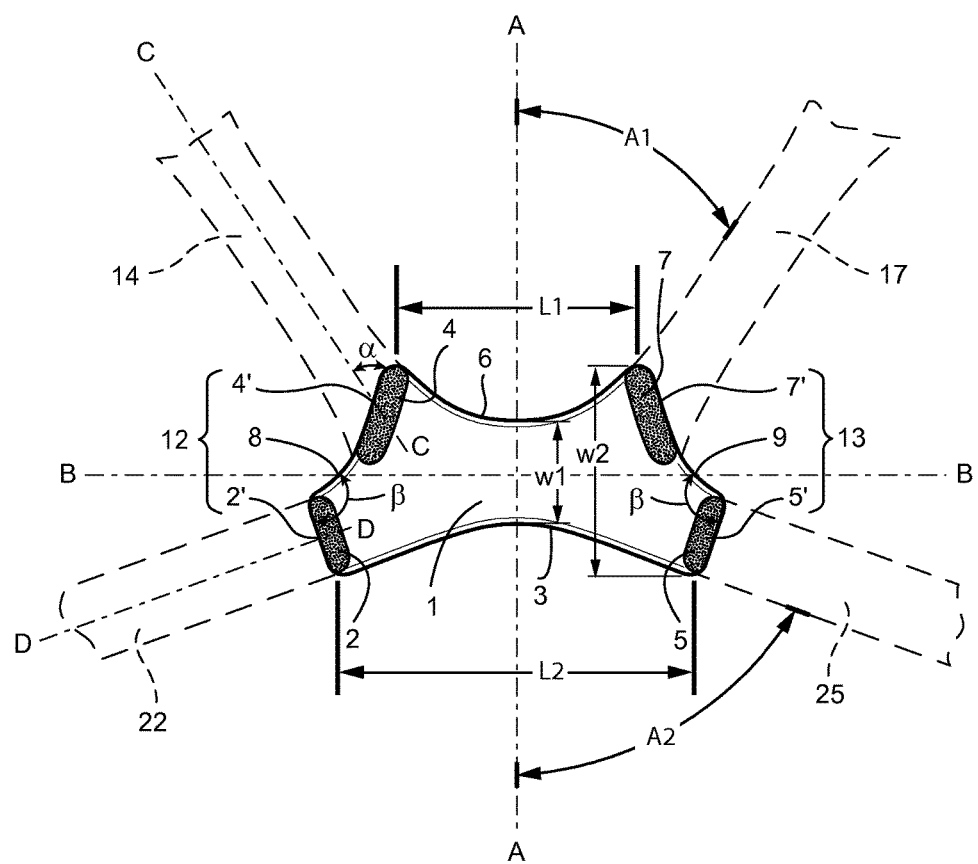

FIG. 6 is an enlarged schematic rear view of a neck portion of the headgear shown in FIG. 5.

Figure 7A:
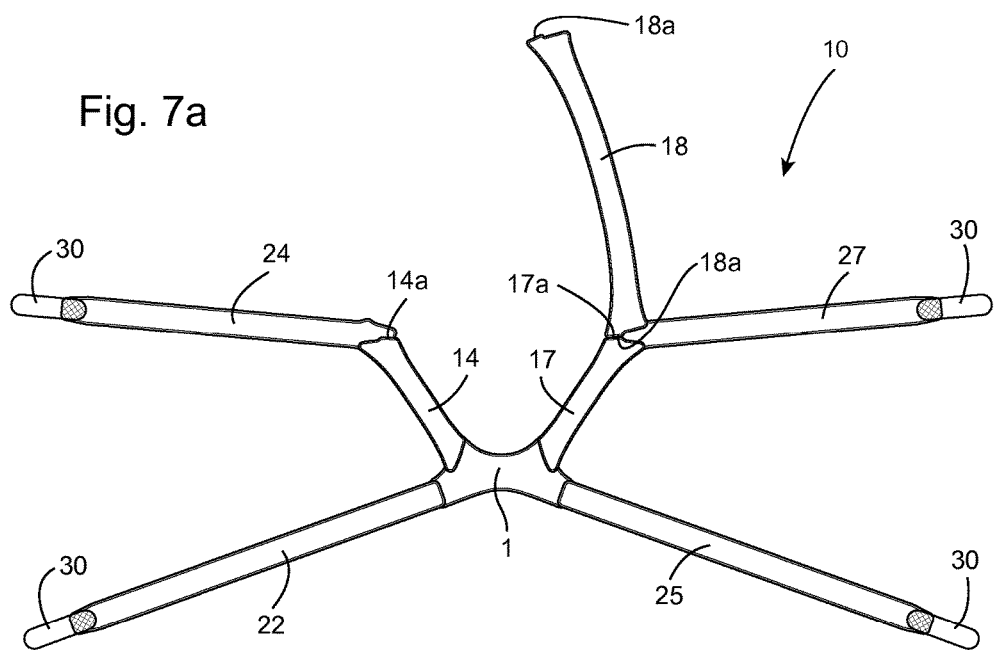
Figure 7B:
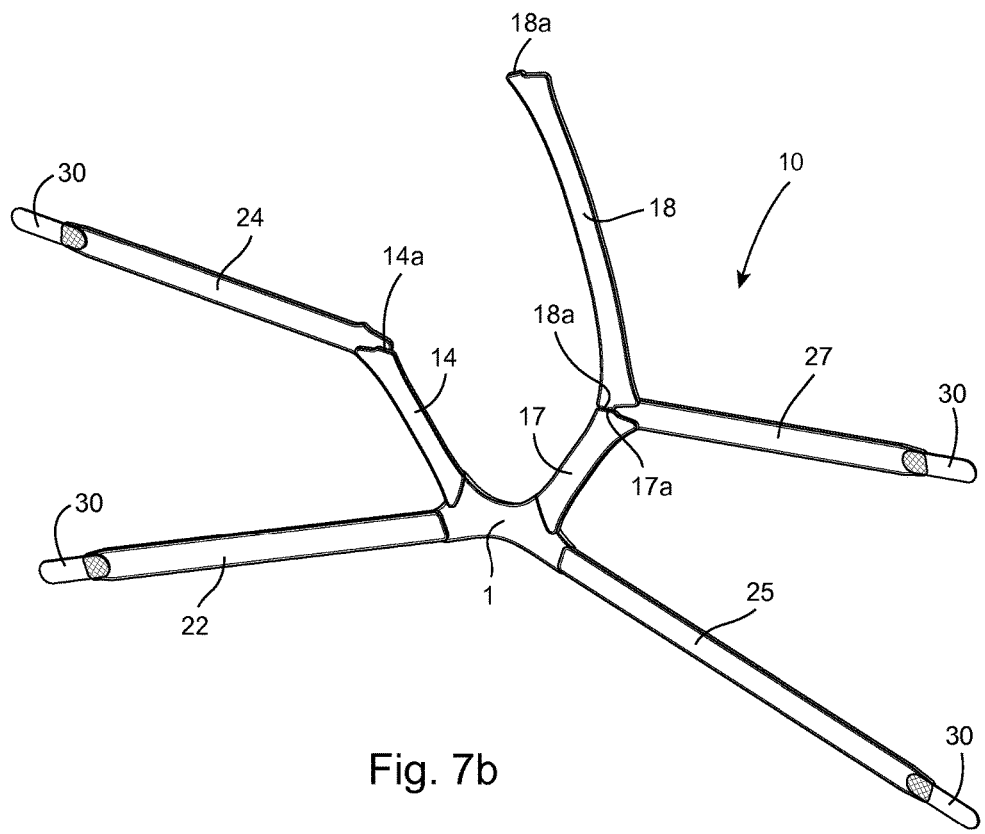

FIGS. 7a and 7b are rear plan and perspective views of the headgear shown in FIG. 5.

Figure 8A:
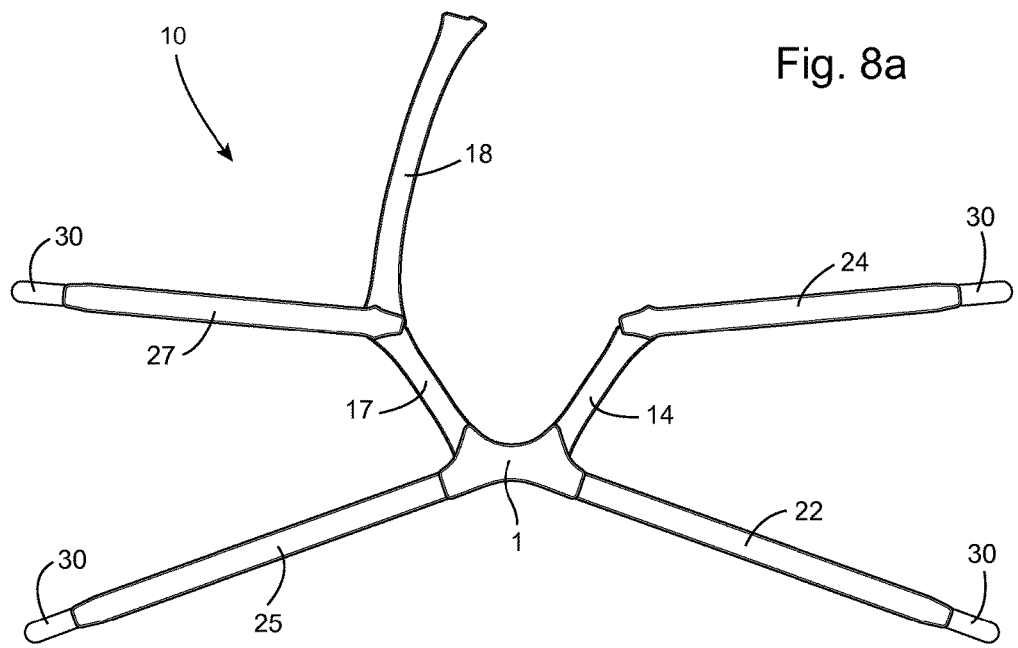
Figure 8B:
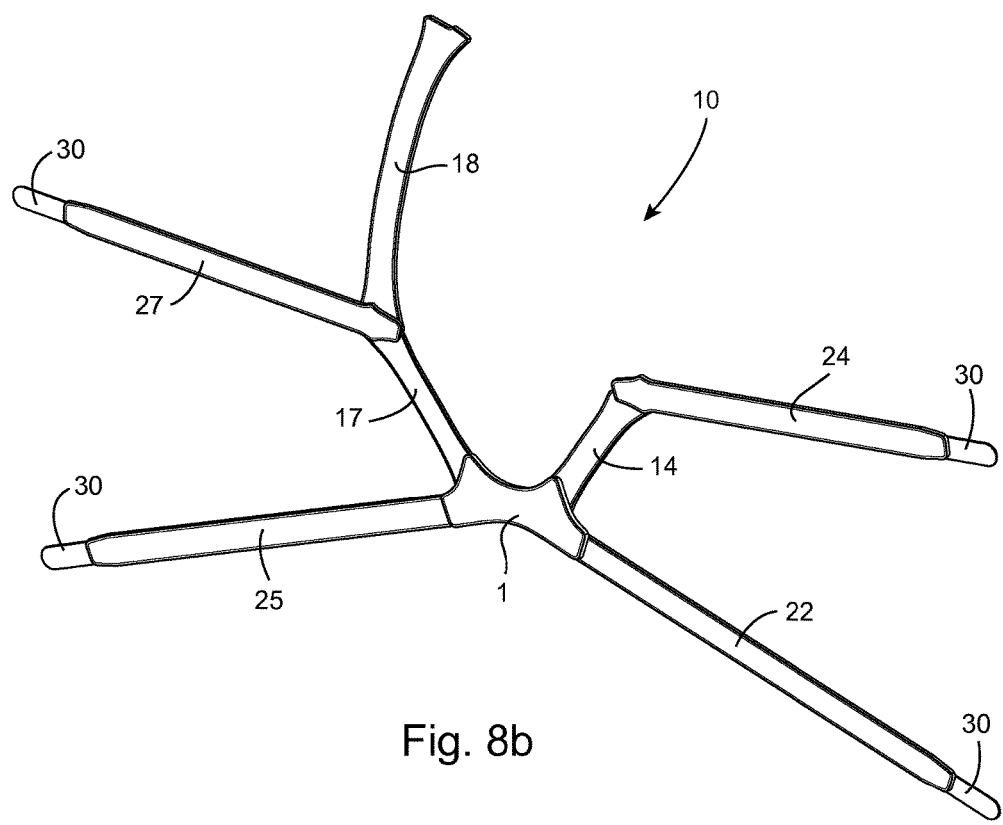

FIGS. 8a and 8b are front plan and perspective views of headgear shown in FIG. 5.

Figure 9:
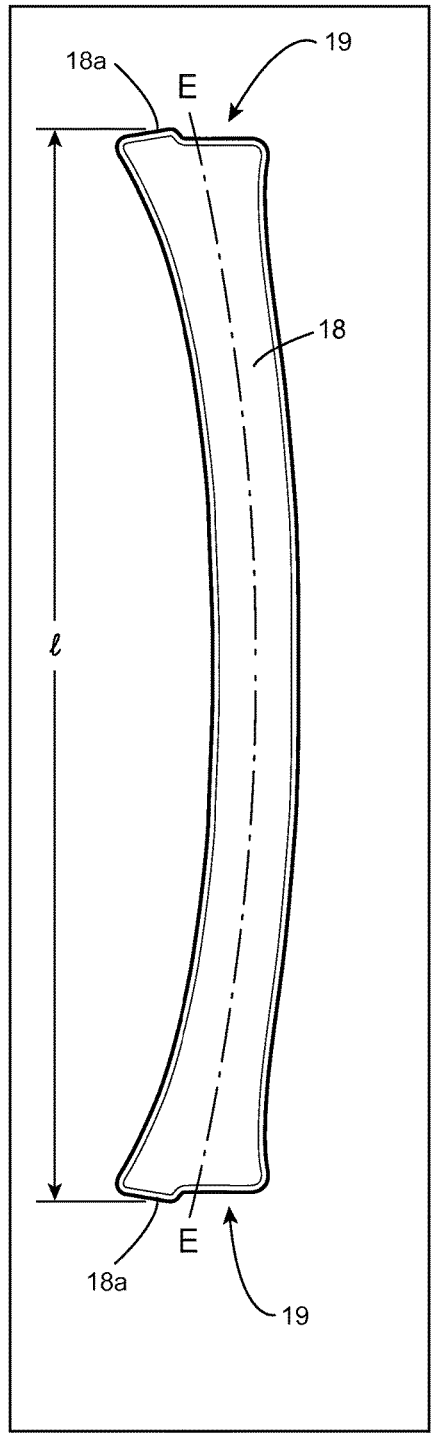

FIG. 9 shows a top crown strap of a crown strap assembly according to an example of the present technology.

Figure 10:
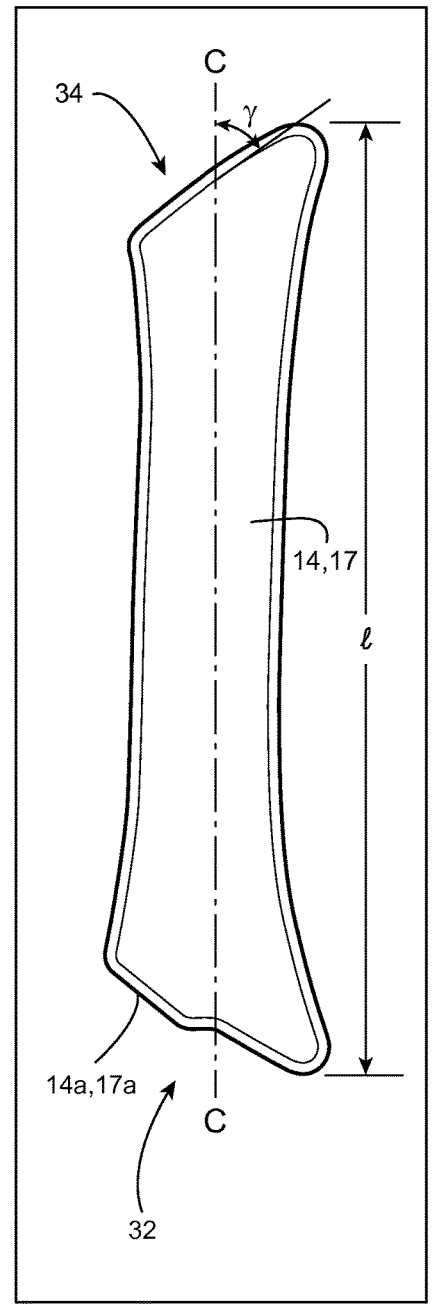

FIG. 10 shows a lateral crown strap of a crown strap assembly according to an example of the present technology.

Figure 11:
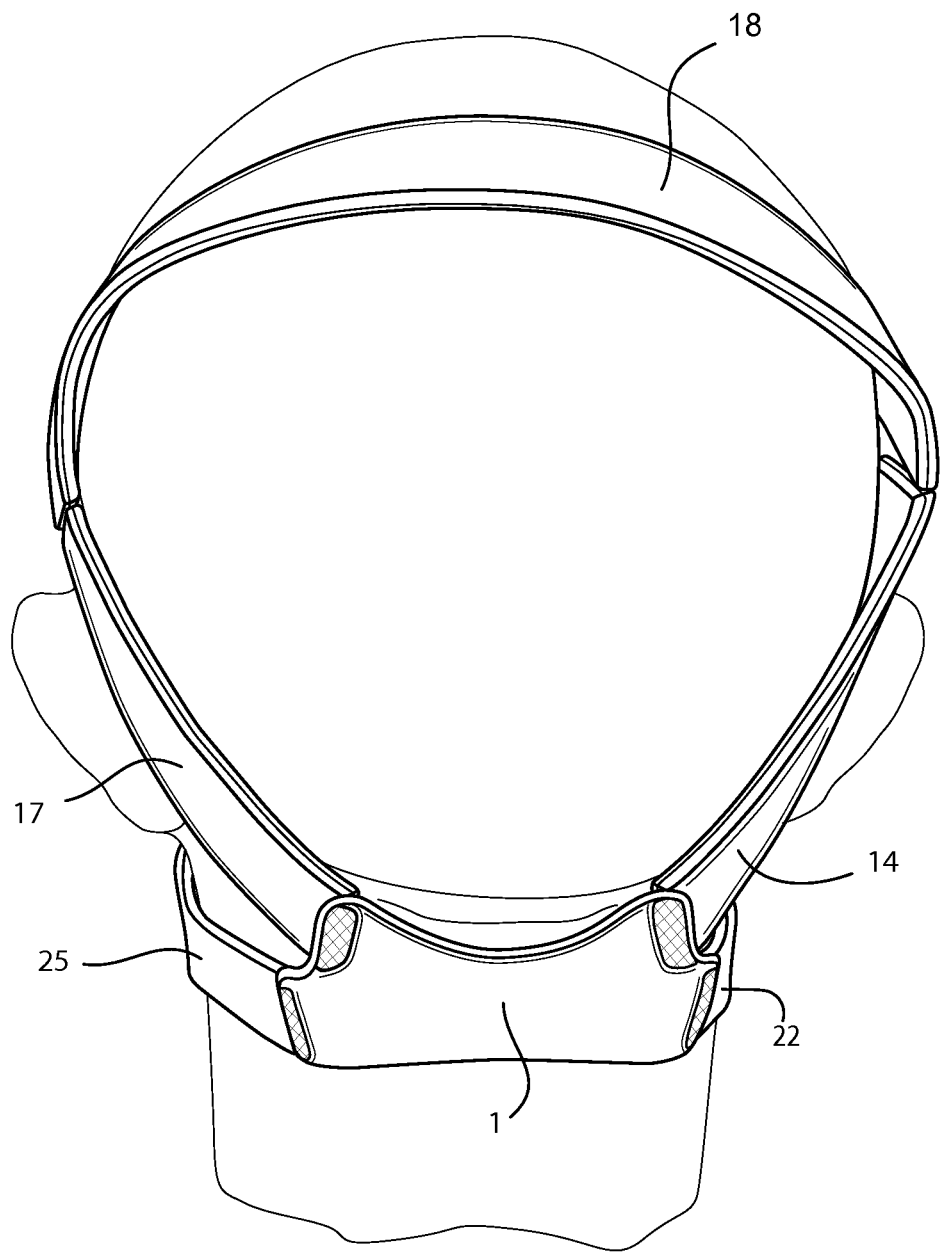

FIG. 11 is a rear view showing headgear according to an example of the present technology in use on a patient with a full-face mask.

Figure 12:
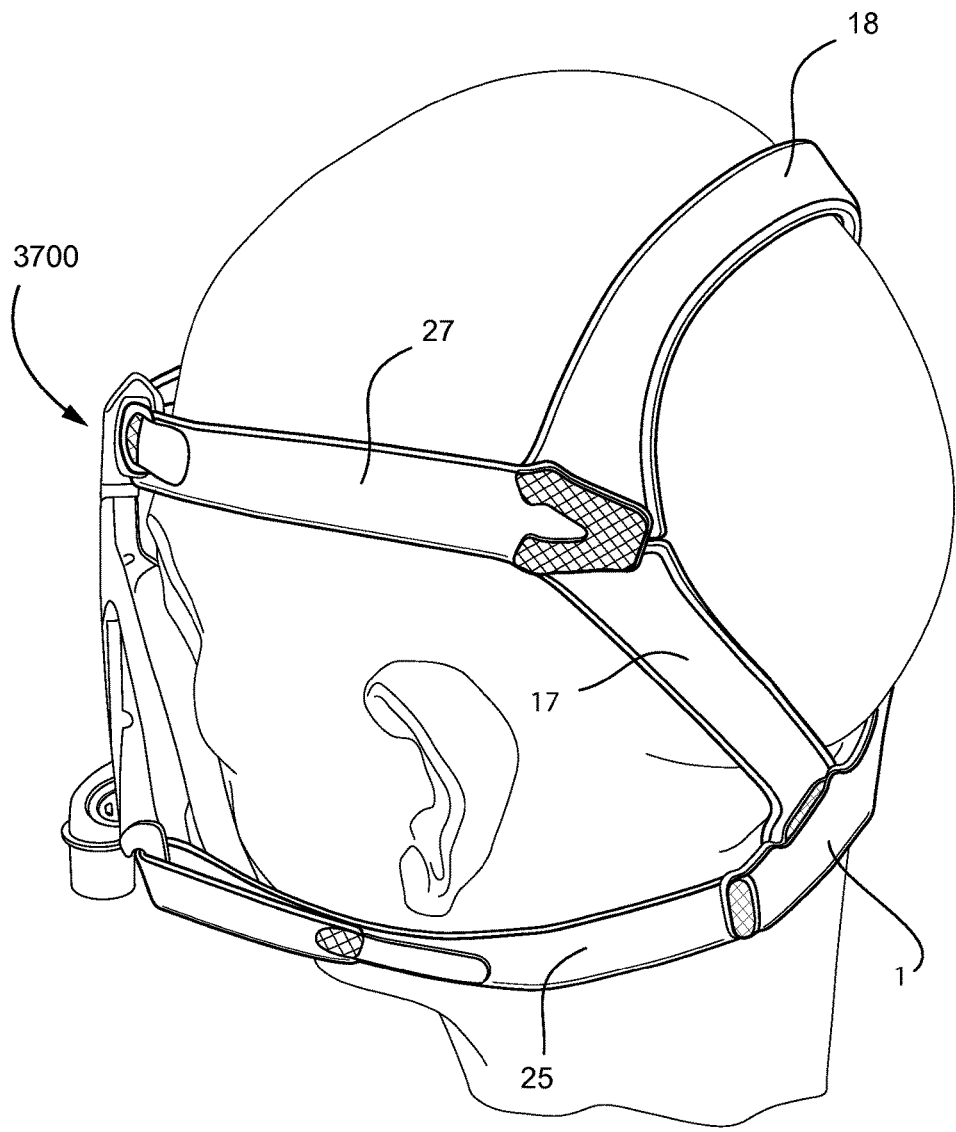

FIG. 12 is a rear side perspective view showing headgear according to an example of the present technology in use on a patient with a full-face mask.

Figure 13:
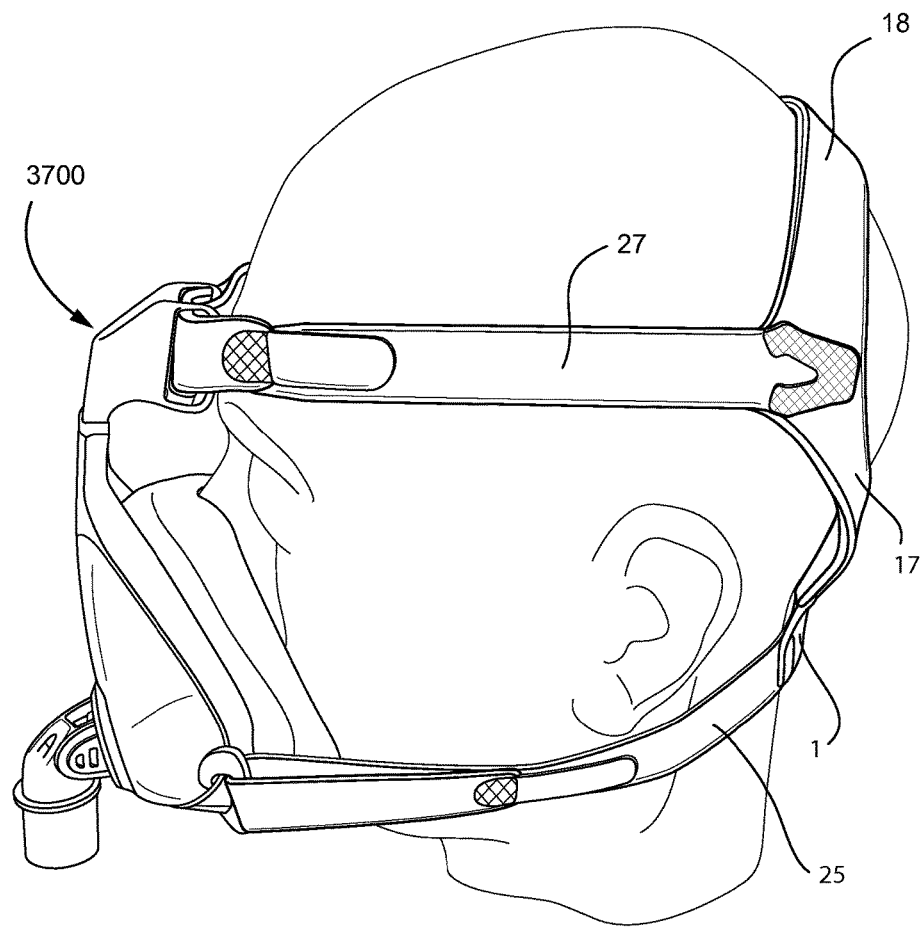

FIG. 13 is a side view showing headgear according to an example of the present technology in use on a patient with a full-face musk.

Figure 14:
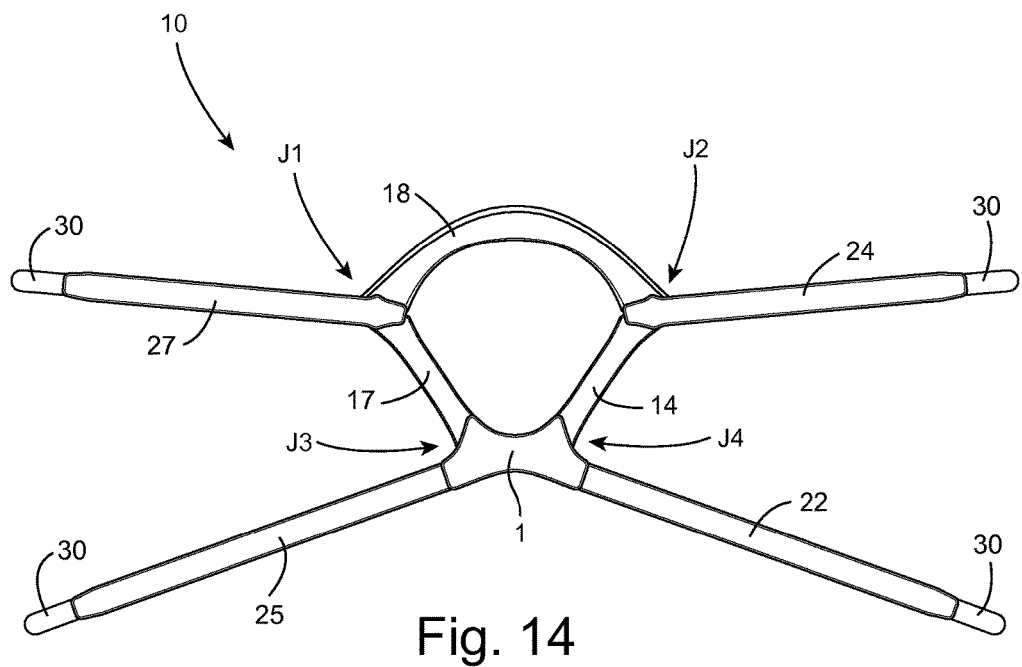

FIG. 14 is a rear view of headgear according to an example of the present technology.

5. DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to several examples which may share one or more common characteristics and features. It is to be understood that one or more features of any one example may be combinable with one or more features of another example or other examples. In addition, any single feature or combination of features in any of the examples may constitute a further example.

5.1 Treatment Systems

Figure 1A:
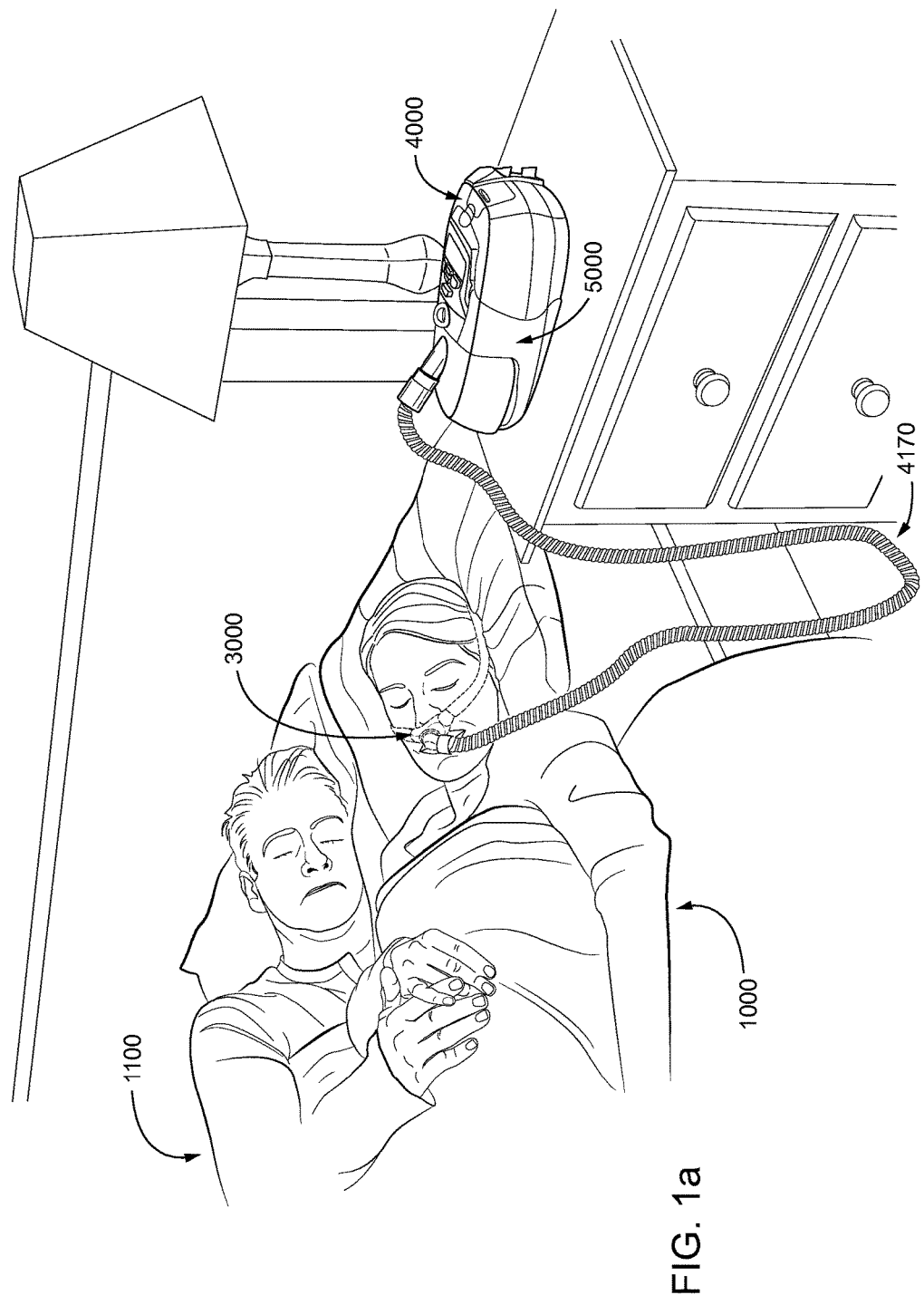
FIG. 1b shows a PAP device in use on a patient with a nasal mask.
FIG. 1c shows a PAP device in use on a patient with a full-face mask.
Figure 1B:
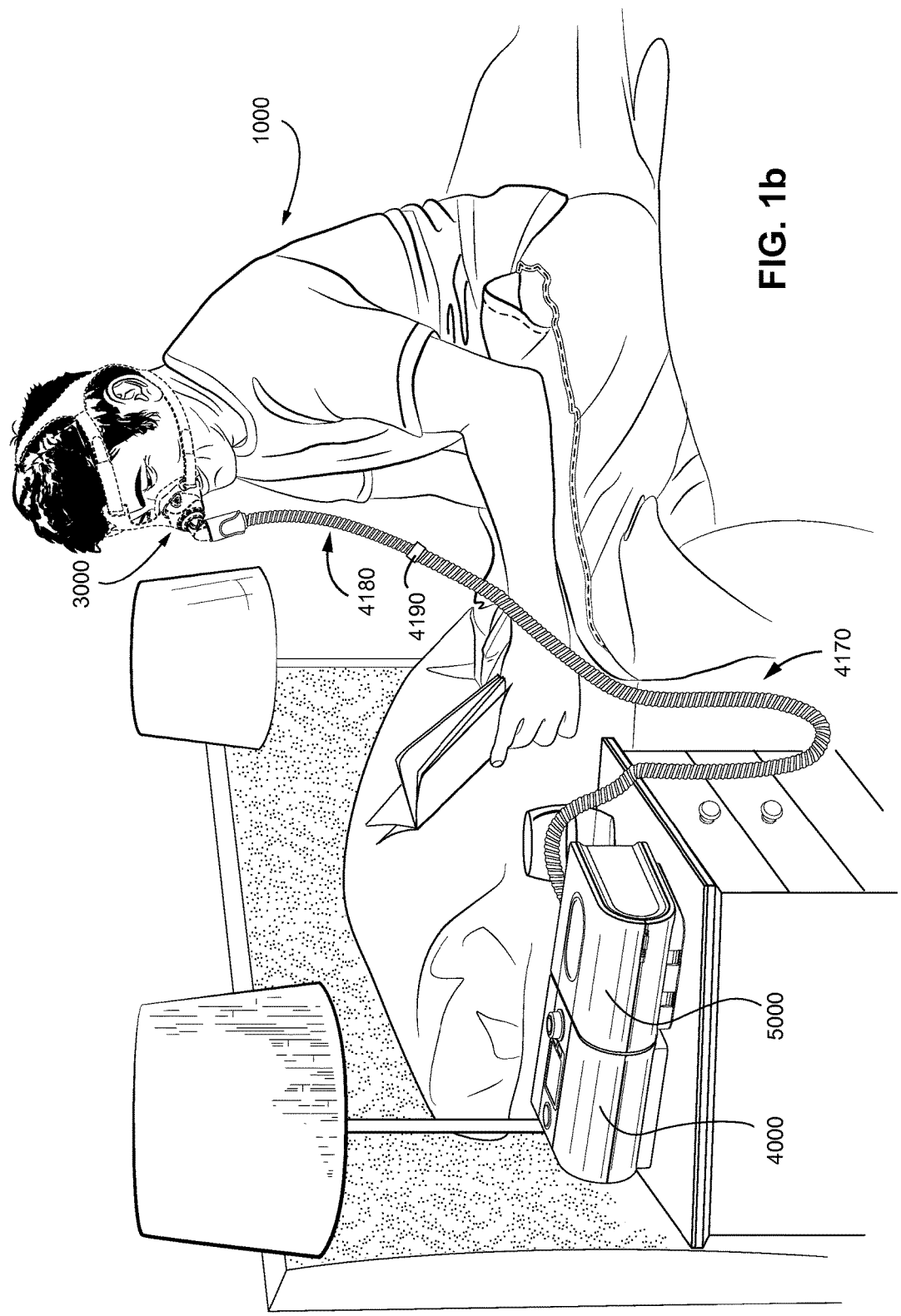
Figure 1C:

In one form, the present technology comprises apparatus for treating a respiratory disorder, as shown in FIGS. 1a-1c. The apparatus may comprise a flow generator or blower for supplying pressurised respiratory gas, such as air, to the patient 1000 via an air delivery tube 4170 leading to a patient interface 3000. The gas delivery tube 4170 may be connected to an additional gas delivery tube 4180 by a rotatable adapter 4190. A humidifier 5000 may also be provided to humidify the gas. A bed partner 1100 may also be present with the patient 5.2 Therapy In one form, the present technology comprises a method for treating a respiratory disorder comprising the step of applying positive pressure to the entrance of the airways of a patient 1000.

5.2.1 Nasal CPAP for OSA

In one form, the present technology comprises a method of treating Obstructive Sleep Apnea in a patient by applying nasal continuous positive airway pressure to the patient.

In certain embodiments of the present technology, a supply of air at positive pressure is provided to the nasal passages of the patient via one or both nares.

In certain embodiments of the present technology, mouth breathing is limited, restricted or prevented.

5.3 Patient Interface 3000

FIG. 4a shows a non-invasive patient interface 3000 in accordance with one aspect of the present technology comprises the following functional aspects: a seal-forming structure 3100, a plenum chamber 3200, a positioning and stabilising structure 3300 and a connection port 3600 for connection to air circuit 4170. In some forms a functional aspect may be provided by one or more physical components. In some forms, one physical component may provide one or more functional aspects. In use the seal-forming structure 3100 is arranged to surround an entrance to the airways of the patient so as to facilitate the supply of air at positive pressure to the airways.

5.3.1 Seal-Forming Structure 3100

In one form of the present technology, a seal-forming structure 3100 provides a sealing-forming surface, and may additionally provide a cushioning function.

A seal-forming structure 3100 in accordance with the present technology may be constructed from a soft, flexible, resilient material such as silicone.

In one form, the seal-forming structure 3100 comprises a sealing flange and a support flange. Preferably the sealing flange comprises a relatively thin member with a thickness of less than about 1 mm, for example about 0.25 mm to about 0.45 mm, that extends around the perimeter of the plenum chamber 3200. Support flange may be relatively thicker than the sealing flange. The support flange is disposed between the sealing flange and the marginal edge of the plenum chamber 3200, and extends at least part of the way around the perimeter. The support flange is or includes a spring-like element and functions to support the sealing flange from buckling in use. In use the sealing flange can readily respond to system pressure in the plenum chamber 3200 acting on its underside to urge it into tight sealing engagement with the face.

In one form the seal-forming portion of the non-invasive patient interface 3000 comprises a pair of nasal puffs, or nasal pillows, each nasal puff or nasal pillow being constructed and arranged to form a seal with a respective naris of the nose of a patient.

Nasal pillows in accordance with an aspect of the present technology include: a frusto-cone, at least a portion of which forms a seal on an underside of the patient's nose; a stalk, a flexible region on the underside of the cone and connecting the cone to the stalk. In addition, the structure to which the nasal pillow of the present technology is connected includes a flexible region adjacent the base of the stalk. The flexible regions can act in concert to facilitate a universal joint structure that is accommodating of relative movement—both displacement and angular—of the frusto-cone and the structure to which the nasal pillow is connected. For example, the frusto-cone may be axially displaced towards the structure to which the stalk is connected.

In one form the non-invasive patient interface 3000 comprises a seal-forming portion that forms a seal in use on an upper lip region (that is, the lip superior) of the patient's face.

In one form the non-invasive patient interface 3000 comprises a seal-forming portion that forms a seal in use on a chin-region of the patient's face.

5.3.2 Plenum Chamber 3200

Preferably the plenum chamber 3200 has a perimeter that is shaped to be complementary to the surface contour of the face of an average person in the region where a seal will form in use. In use, a marginal edge of the plenum chamber 3200 is positioned in close proximity to an adjacent surface of the face. Actual contact with the face is provided by the seal-forming structure 3100. Preferably the seal-forming structure 3100 extends in use about the entire perimeter of the plenum chamber 3200.

5.3.3 Vent 3400

In one form, the patient interface 3000 includes a vent 3400 constructed and arranged to allow for the washout of exhaled carbon dioxide.

One form of vent 3400 in accordance with the present technology comprises a plurality of holes, for example, about 20 to about 80 holes, or about 40 to about 60 holes, or about 45 to about 55 holes.

Preferably the vent 3400 is located in the plenum chamber 3200. Alternatively, the vent 3400 is located in a decoupling structure 3500, e.g. a swivel.

5.3.4 Decoupling Structure(s) 3500

In one form the patient interface 3000 includes at least one decoupling structure 3500, for example a swivel or a ball and socket.

5.3.5 Connection Port 3600

Connection port 3600 allows for connection to the air circuit 4170.

5.3.6 Forehead Support 3700

In one form, the patient interface 3000 includes a forehead support 3700.

5.3.7 Anti-Asphyxia

In one form, the patient interface 3000 includes an anti-asphyxia valve.

5.3.8 Ports

In one form of the present technology, a patient interface 3000 includes one or more ports, that allow access to the volume within the plenum chamber 3200. In one form this allows a clinician to supply supplemental oxygen. In one form this allows for the direct measurement of a property of gases within the plenum chamber 3200, such as the pressure.

5.3.9 Positioning and Stabilizing Structure 3300

In an example, the seal-forming portion 3100 of the patient interface 3000, e.g., breathing mask (e.g., nasal mask, mouth mask, or a full-face mask for PAP therapy), of the present technology is held in sealing position in use by the positioning and stabilising structure 3300.

FIG. 5 depicts a front perspective view of a positioning and stabilizing structure in the form of headgear 10 according to an example of the present technology. The headgear 10 includes a crown assembly or crown strap assembly 15, upper connection straps or upper mask connection straps 24, 27 provided to the crown assembly 15 and adapted to connect to upper headgear connectors of the patient interface, and lower connection straps or lower mask connection straps 22, 25 provided to the crown assembly 15 and adapted to connect to lower headgear connectors of the patient interface. Crown assembly 15 comprises neck strap 1, lateral crown straps 14, 17 and top crown strap 18. Neck strap 1 is connected to lateral crown straps 14, 17 as well as to lower connection straps 22, 25. Lateral crown straps 14, 17 and top crown strap 18 are connected in thinned connecting portions 14a. 17a. 18a (e.g., see FIGS. 7a and 7b) providing increased flexibility. In the illustrated example, the connecting portions 14a, 17a. 18a are arranged in an at least partly overlapping fashion on the upper connection straps 24, 27 as shown in FIGS. 7a and 7b. The connecting portions 14a, 17a, 18a may have a V-shape and may be at least partially spaced apart from each other. The connecting portions 14a, 17a, 18a may be welded portions. The upper and lower connection straps 24, 27, 22, 25 are each provided with adjustment or fastening members 30, e.g., hook and loop materials.

As noted above, the top crown strap 18 and the lateral crown straps 14, 17 may be connected at and/or via portions of the upper mask connection straps 24, 27. Such joints may be constructed as a thinned region or thinned connection portions 14a, 17a. 18a to encourage bending. The thinned region may function as a flex point or hinge (e.g., a living hinge) to provide increased flexibility where desired. The flex point or hinge may be reinforced using hot-melt seam tape, or a thinner fabric layer with an adhesive backing, or other reinforcement methods. Such a hinge feature of the connection may permit the headgear to better accommodate the shape of a patient's head. A combination of linear and nonlinear joints may be utilized to achieve a desired level of flexibility and direction of flexion, as well as a desired level of three dimensional shaping to a component made up of a series of parts which were originally a flat material (such as fabric or paper, for example). Such shaping may include darts, tucks, gathers, or a curved seam. An example joint is depicted in FIG. 3-2 of WO2013/026092 A1 which is hereby incorporated by reference.

In an example, as shown in FIGS. 5 and 11-13, the crown strap assembly 15 may have a generally round three-dimensional shape adapted to cup the parietal hone and occipital bone of the patient's head in use. The crown strap assembly may have a three-dimensional contour curve substantially to fit to the shape of a user's crownback of a user's head. The straps 1, 14, 17, 18 may at least partially not extend in the same plane thereby forming a three-dimensional shape of the crown strap assembly 15. The top crown strap 18 may be located on the top of the crown in the application position. The top crown strap 18 may extend between the upper connection straps 24, 27. As shown in FIGS. 11-13, the upper connection straps 24, 27 may extend to the forehead region of the user, e.g., to connect to upper headgear connectors of a forehead support of the patient interface. In the application position, the neck strap 1 may form the lower part of the ring-like crown strap assembly 15.

In the illustrated example, the top crown strap 18 and the lateral crown straps 14, 17 may be configured as separate elements. The separate elements may be joined together during the manufacturing process. Alternatively, the top crown strap and the lateral crown straps 14, 17 may be configured as or made of one piece. In one example, the top crown strap 18 and the lateral crown straps 14, 17 may be cut out of one material sheet.

In the illustrated example, the headgear 10 includes 8 separate straps that are connected (e.g., ultrasonically welded) to one another to construct the headgear adapted for use with the patient interface. For example, as shown in FIG. 14, the crown strap assembly 15 includes 4 separate straps (top crown strap 18, lateral crown straps 14 and 17, and neck strap 1) that are connected to one another in 4 junction points, J1, J2, J3, and J4. Two of the junction points J1 and J2 (referred to as top junction points) at the top of the headgear join together three of the straps from the crown strap assembly (i.e., the top crown strap 18 and the lateral crown straps 14 and 17) and the upper mask connection straps 24 and 27. The other two junction points J3 and J4 (referred to as neck junction points) at the bottom of the headgear join the lateral crown straps 14 and 17 together at opposite ends of the neck strap 1. The neck strap 1 may be separately connected (e.g., welded) to the lower mask connection straps 22 and 25.

This arrangement allows the crown strap assembly 15 to be formed from three substantially rectangular crown strap pieces (i.e., top crown strap 18 and lateral crown straps 14 and 17) and then connected (e.g., ultrasonically welded) together via the junction points with the neck strap 1 to form the three-dimensional contoured shape adapted to fit the back of the patient's head in use.

Designing the crown strap pieces (i.e., top crown strap 18, lateral crown straps 14 and 17, and neck strap 1) separately may allow flexibility for the crown strap pieces to be made relatively smaller which contributes to an increased yield and simpler process of manufacturing. In addition, the design of the crown strap pieces may allow for less material wastage when cut from a sheet, e.g., due to the substantially rectangular shape of the crown straps 14, 17, and 18. Moreover, manufacturing the crown strap assembly in separate pieces may allow for the substitution of materials that are less expensive, more comfortable and/or have an aesthetically pleasing color.

However, in an alternative example, two or more straps may be configured as or made of one piece. For example, as noted above, the top crown strap 18 and the lateral crown straps 14 and 17 may be configured as one piece. Also, in an example, the neck strap 1 and the lower mask connection straps 22 and 25 may be configures as one piece.

FIG. 6 is an enlarged view of a neck strap 1 according to an example of the present technology. In an example, the neck strap may be substantially flat. In an example, the neck strap 1 provides a one-piece main body that is a separate and distinct structure from the remaining straps of the headgear.

The main body of the neck strap 1 comprises two opposing major side edges or major side surfaces 3, 6. In the illustrated example, the major side edges 3, 6 each have a generally curved shape, i.e., curved or arc-shaped portion. As illustrated, the curved shape or curvature may be concave. The major side edges 3, 6 interconnect two minor side edges or minor side surfaces 12, 13 of the main body.

Axis A-A is located in the axis of symmetry of neck strap 1. In the illustrated example, the neck strap 1 is symmetrical to the axis A-A, wherein the axis A-A in the application position is substantially parallel. e.g., parallel, to the sagittal plane, e.g., to the median plane, of a user.

The two minor side edges 12, 13 are located remotely or laterally spaced from the axis A-A. The first minor side edge 12 comprises three edge portions, i.e., first lower connection edge portion 2', first upper connection edge portion 4', and first transitional edge portion 8. First lower connection edge portion 2' is a portion that extends substantially parallel to an adjacent first lower connection portion 2 of neck strap 1. First upper connection edge portion 4' extends substantially parallel to an adjacent first upper connection portion 4 of neck strap 1. First transitional edge portion 8 interconnects the first upper connection edge portion 4' with the first lower connection edge portion 2'.

The second minor side edge 13 is symmetrical to the first minor side edge 12 and also comprises three edge portions, i.e., second lower connection edge portion 5', second upper connection edge portion 7', and second transitional edge portion 9. The second upper and lower connection edge portions 7', 5' as well as second transitional edge portion 9 are arranged in the same fashion as the first upper and lower connection edge portions 4', 2' and the first transitional edge portion 8. For example, the second lower connection edge portion 5' is a portion that extends substantially parallel to an adjacent second lower connection portion 5 of neck strap 1, and the second upper connection edge portion 7' extends substantially parallel to an adjacent second upper connection portion 7 of neck strap 1.

The first transitional edge portion 8 intersects with first lower connection edge portion 2' in an angle β, e.g., between 60° to 120°, between 75° to 105°, approximately 90°, whereas the upper connection edge portion 4' intersects with the transitional edge portion 8 in a tangential fashion. Similarly, the second transitional edge portion 9 intersects with the lower connection edge portion 5' in an angle β, e.g., between 60° to 120°, between 75° to 105°, approximately 90°, whereas the upper connection edge portion 7' intersects with the transitional edge portion 9 in a tangential fashion.

In the illustrated example, the neck strap 1 provides a one-piece main body that eliminates a joint in the sagittal or median plane. Thus, no stitch is provided in the plane through the middle of the patient's head in use. A stitch in that area of the neck may be uncomfortable. Having no joint in that area may also allow the width of the neck strap in that area to be reduced, which may lead to a reduced overall footprint. The material costs may also be reduced. In addition, the positioning of the straps may be further improved and the overall shape of the headgear may be better adapted to the average patient.

As shown in FIG. 6, the width of neck strap 1 may have at least a partially reduced width between opposing major side edges 3, 6, particularly the width w1 is reduced or lowest in the concave curved part of opposing major side edges 3, 6, measured in a direction perpendicular to axis B-B. Axis B-B itself is an axis perpendicular to axis A-A. In an example, the width w1 may be in the range of about 22-25 mm, e.g., about 24 mm. The width w2 perpendicular to the axis B-B may be highest at a cross-section in which a major side edge 3, 6 intersects with a minor side edge 12, 13, e.g., in which a major side edge 3, 6 intersects with the first or second upper connection edge portion 4', 7' or the first or second lower connection edge portion 2', 5'. In an example, the width w2 may be in the range of about 42-26 mm, e.g., about 45 mm. In an example, at least one major side edge 3, 6 and/or at least one minor side edge 12, 13 may be rounded.

According to an example of the present technology, the neck strap 1 includes a relatively smaller size and includes a curvature along the upper and lower major side edges 3, 6 to enhance comfort and mobility. In an example, as shown in FIG. 6, the neck strap 1 may include a length L1 in the range of about 55-60 mm, e.g., 58 mm, and a length 12 of about 82-90 mm, e.g., 86 mm. Also, in an example, as shown in FIG. 6, the major side edge 6 may define an angle A1 in the range of about 30-40°, e.g., 34°, and the major side edge 3 may define an angle A2 in the range of about 65°-75°, e.g., 70°.

As best shown in FIGS. 11-13, the smaller size and the curvature in the upper and lower side edges 3, 6 of the neck strap 1 allow for additional head mobility by a patient in use. For example, the smaller overall size of the neck strap 1 and its curvature in the upper edge 3 provide additional spacing between the occiput of the patient and the upper edge 3 such that a patient may bend their head backwards towards their spine (e.g., in a posterior direction) with an additional freedom of movement while avoiding contact between the upper edge 3 and the patient's occiput. Contact of the patient's occiput with the upper edge 3 of the headgear may cause discomfort and may also apply additional force on the mask connection straps 22, 24, 25, 27, which ultimately impacts the force applied to the patient by the patient interface and sealing forming structure. Thus, the additional spacing provided by size and curvature of the neck strap 1 provides additional mobility without impacting the back of the patient's neck and the force applied to the patient by the patient interface and sealing forming structure.

Lateral crown straps 14, 17 indicated by dotted lines in FIG. 6 are connected or connectable to neck strap 1 in respective first and second upper connection portions 4, 7. Lower connection straps 22, 25 depicted in dotted lines in FIG. 6 are connected or connectable to neck strap 1 in respective first and second lower connection portions 2, 5. First and second lower connection portions 2, 5 and the first and second lower connection edge portions 2', 5' of the illustrated example extend generally perpendicular to the main axis of extension D-D of respective lower connection straps 22, 25. In the illustrated example, the first and second upper connection portions 4, 7 and the first and second upper connection edge portions 4', 7' are each oriented in an acute angle α to the main axis of extension C-C of respective first and second lateral crown straps 14, 17 to be connected to the neck strap.

In an example, the first and/or second lower connection straps 22, 25 and the neck strap 1 may be configured as one piece, e.g., cut out of one material sheet. Such a one piece neck strap may be connected via upper first and/or second connection portions 4, 7 to the lateral crown straps 14, 17. In such example, the costs for welding may be reduced while the material waste may only be moderately increased if at all.

FIGS. 7a and 7b show rear views, and FIGS. 8a and 8b show front views of the headgear 10 according to an example of the present technology. Each connection strap 24, 27, 22, 25 is provided with an adjustment or fastening member 30, e.g., a hook fastener. The headgear or headband in FIGS. 7a, 7b, 8a, and 8b is depicted before the final assembly step. By connecting, e.g., welding, the top crown strap 18 to the upper connection strap 24 and/or the lateral crown strap 14, the final three-dimensional crown assembly 15 is obtained. For example, the thinned connecting portion 18a of the top crown strap 18 may be connected to the thinned connecting portion 14a of the lateral crown strap 14, and the thinned connection portion 18a may be arranged in at least partly overlapping fashion on the upper connection strap 24.

FIG. 9 shows the (substantially) elongated shape of a top crown strap 18 according to an example of the present technology. As illustrated, the top crown strap 18 comprises a substantially curved main axis E-E (i.e., main axis E-E substantially extends as a curved line) and stepped front sides 19 at both ends. Each of the stepped front sides or stepped portion 19 provides a thinned connection portion 18a adapted to connect to the lateral crown straps 14, 17 and the upper connection straps 24, 27.

FIG. 10 shows a lateral crown strap 14, 17 according to an example of the present technology. As illustrated, each lateral crown strap 14, 17 includes one stepped front side or front end wall 32, one flat or smooth front side or front end wall 34, and a generally straight main axis C-C. The stepped front side or stepped portion 32 provides a thinned connection portion 14a, 17a adapted to connect to the top crown strap 18 and the upper connection straps 24, 27. Each front side 32, 34 extends in an acute angle γ to the strap's main axis C-C. In an example, the acute angle γ may be substantially equal to the acute angle α of the first and second upper connection portions 4, 7 and/or the adjacent first and second upper connection edge portions 4', 7' of the minor side edges 12, 13 to the lateral crown strap's main axis C-C.

The lateral crown straps 14, 17 may be located on either side of the crown in the application position. As best shown in FIGS. 7a to 8b, the lateral crown straps 14, 17 and/or the neck strap 1 may be arranged so as to build a V-shape in a plane view and/or in the application position. The top crown strap 18 and/or at least one of the lateral crown straps 14, 17 may be strap elements having a substantially elongated shape. In an example, a "substantially elongated" strap is a strap with slightly arc-shaped sides. A deviation from the rectangular shape in a width direction may be less than twice the width of the strap. In an example, a strap having a significant L-shape or a significantly curved shape may not be considered as a substantially elongated strap. Substantially elongated straps advantageously reduce the material waste. In an example, the lateral crown straps 14, 17 may have substantially the same length, and the lateral crown straps 14, 17 may have a mirror-inverted shape. At least one end of each lateral crown strap 14, 17 may have an increased width compared to another portion of the respective strap.

In an example, the width of the top crown strap 18 of FIG. 9 may be different compared to the width of the lateral crown straps 14, 17, e.g., the width of the top crown strap 18 may be thinner than the width of the lateral crown straps 14, 17. Also, in an example, the length of the top crown strap 18 of FIG. 9 may be different compared to the length of the lateral crown straps 14, 17, e.g., the length of the top crown strap 18 may be longer than the length of the lateral crown straps 14, 17. For example, the length l of the top crown strap 18 in FIG. 9 may be in the range of about 218-222 mm, e.g., 220 mm, and the length l of the lateral crown straps 14, 17 in FIG. 10 may be in the range of about 113-117 mm, e.g., 115 mm.

Also, in an example, the width of the top crown strap 18 and/or lateral crown straps 14, 17 may, at least partially, be reduced compared to the width of at least one of the mask connection straps 22, 24, 27, 30. Accordingly, the footprint may be further reduced and the material usage may be reduced too. The width of the top, lateral or neck straps, 18, 14, 17, 1 and thus the footprint may be additionally reduced by using different materials, different strap thicknesses and/or different compositions. Different materials and/or cheaper materials may be used for some parts or portions of a headgear, e.g., with the same seal support efficacy and/or comfort. In an example, the neck strap 1 may have an increased thickness compared to the lower mask connection straps 22, 25. This may increase comfort.

In an example, at least two straps selected from the group of mask connection straps 22, 24, 25, 27, top crown strap 18, lateral crown straps 14, 17, and/or neck strap 1 may be made of a different material. In an example, at least one of the mask connection straps 22, 24, 25, 27 is made of a different material compared to the top crown strap 18 and/or the two lateral crown straps 14, 17. The neck strap 1 may be made of a different material compared to the top crown strap 18, at least one of the lateral crown straps 14, 17 and/or at least one upper and/or lower mask connection strap 22, 24, 25, 27. At least one strap selected from the group of mask connection straps 22, 24, 25, 27, top crown strap 18, lateral crown straps 14, 17, and/or neck strap 1 may at least partially be made of or comprise nylon and/or lycra. At least a portion of the top crown strap 18, the lateral crown straps 14, 17 and/or the neck strap 1 may comprise different layers, e.g., of different materials. Different layers may be welded one to another. In an example, the strap may comprise different layers of different materials, e.g. an outer layer of an aesthetically pleasing material and/or an inner layer facing the patients head in an application position made of a soft and/or pleasing material. For example, the straps forming the crown assembly 15 may be made of an inexpensive and/or comfortable material. In an example, different materials for different layers of a strap portion and/or different straps may be selected depending on the specific properties/functions/requirements. In an example, the headgear may be BPA-free and Gelamid® may be applied at least for portions of the strap. All above straps may be cut of a sheet material by ultrasonic cutting.

In an example, a strap may be a single layer component such as a textile or fabric, or a composite or multiple layer components such as fabric and foam composites, or outer fabric layers and inner spacer fabrics. The straps may be made of a spandex or clastane/foam composite, or may be formed of other suitable materials (such as a 3D spacer fabric or a double-knit interlock fabric). These straps may be cut from a sheet of material (e.g., flame laminated), or cut from a roll of narrow fabric strap and then thermoformed and ultrasonically welded to create rounded edges before being ultrasonically welded together. The straps may have a geometry that allows them to be nested on the sheet to increase yield, e.g., the geometry may be substantially linear.

In some examples, tape may be overlaid with a thin fabric layer having a thickness of about 0.1 mm and about 1 mm to maintain a desirable soft surface finish. Such thermoplastic sheets may be made from, for example: polyurethane (TPU), polyester, polyamide, polyolefin and aliphatic urethanes. These materials may be customized to provide the optimum performance characteristics for specific applications, and may be produced in a range of colors, opacities, and surface finishes desired for the end use of patient interface equipment for the treatment of sleep disordered breathing, such as in headgear or a mask arrangement. Materials having differing degrees of flexibility may be combined in an alternating manner to form a controlled flex region. Components may be stacked one on top of the other and ultrasonically welded together in a manner that leaves no space therebetween. The patient interface component may be constructed of a soft material, e.g., a soft fabric.

In an example, the thickness of the top crown strap 18 and/or lateral crown straps 14, 17 may be at least partially about 3.8 mm (+−0.5 mm). In an example, the thickness of the neck strap 1 may be at least partially about 4.2 mm (+−0.5 mm). In an example, the thickness of the mask connection straps 22, 24, 25, 27 may be at least partially about 2.5 mm (+−0.5 mm).

In an example, at least two straps selected from the group of mask connection straps 22, 24, 25, 27, top crown strap 18, lateral crown straps 14, 17, and/or neck strap 1 may be connected by welding. e.g., by ultrasonic welding. Exemplary welding is explained in detail in the summary of technology in the publication WO2013/026092 A1 which is incorporated by reference. In particular. FIG. 3-1 and FIG. 3-2 of WO2013/026092 A1 depict an example of the welding of a top crown strap and/or lateral crown straps. In an example, portions of the top crown strap 18 and the upper mask connection straps 24, 27 may overlap and portions of the lateral crown straps 14, 17 and the upper mask connection straps 24, 27 also may overlap. These members may be placed in an ultrasonic welding tool. e.g., such as that disclosed in WO2013/026092. An advantage of the ultrasonic welding process is that a flush or butt joint does not increase the thickness of the components at the joint and is visually appealing, unlike stitching where components must be overlapped and which results in an uneven thickness. Even if the edges of the two or more components are butted together and stitched without any or substantial overlapping, the stitches will create a rougher, stiffened and raised joint. Further, the ultrasonic flush or butt joint may result in a smooth connection that may reduce skin irritation, chaffing or facial marking, even when reinforced with seam reinforcement tape. An advantage of using an overlapped ultrasonic weld variation is that multiple components may be joined in a single machine in one operation. Furthermore, the ultrasonic welding process may be designed such that the joint is embodied as a thinned region or thinned portion between the components.

5.4 PAP Device 4000

A preferred PAP device 4000 in accordance with one aspect of the present technology comprises mechanical and pneumatic components 4100, electrical components 4200 and is programmed to execute one or more algorithms 4300. The PAP device preferably has an external housing 4010, preferably formed in two pans, an upper portion 4012 of the external housing 4010, and a lower portion 4014 of the external housing 4010. In alternative forms, the external housing 4010 may include one or more panel(s) 4015. Preferably the PAP device 4000 comprises a chassis 4016 that supports one or more internal components of the PAP device 4000. In one form a pneumatic block 4020 is supported by, or formed as part of the chassis 4016. The PAP device 4000 may include a handle 4018.

The pneumatic path of the PAP device 4000 preferably comprises an inlet air filter 4112, an inlet muffler, a controllable pressure device capable of supplying air at positive pressure (preferably a blower 4142), and an outlet muffler. One or more pressure sensors and flow sensors may be included in the pneumatic path.

The pneumatic block 4020 may comprise a portion of the pneumatic path that is located within the external housing.

The PAP device 4000 may have an electrical power supply 4210 and one or more input devices 4220. Electrical components 4200 may be mounted on a single Printed Circuit Board Assembly (PCBA) 4202. In an alternative form, the PAP device 4000 may include more than one PCBA 4202.

5.5 Humidifier 5000
5.5.1 Humidifier Overview

In one form of the present technology there is provided a humidifier 5000, as shown in FIG. 3b, that may comprise a water reservoir and a heating plate.

5.6 Glossary

For the purposes of the present technology disclosure, in certain forms of the present technology, one or more of the following definitions may apply. In other forms of the present technology, alternative definitions may apply.

5.6.1 General

Air: In certain forms of the present technology, air supplied to a patient may be atmospheric air, and in other forms of the present technology atmospheric air may be supplemented with oxygen.

Continuous Positive Airway Pressure (CPAP): CPAP treatment will be taken to mean the application of a supply of air or breathable gas to the entrance to the airways at a pressure that is continuously positive with respect to atmosphere, and preferably approximately constant through a respiratory cycle of a patient. In some forms, the pressure at the entrance to the airways will vary by a few centimeters of water within a single respiratory cycle, for example being higher during inhalation and lower during exhalation. In some forms, the pressure at the entrance to the airways will be slightly higher during exhalation, and slightly lower during inhalation. In some forms, the pressure will vary between different respiratory cycles of the patient, for example being increased in response to detection of indications of partial upper airway obstruction, and decreased in the absence of indications of partial upper airway obstruction.

5.6.2 Aspects of PAP Devices

Air circuit: A conduit or tube constructed and arranged in use to deliver a supply of air or breathable gas between a PAP device and a patient interface. In particular, the air circuit may be in fluid connection with the outlet of the pneumatic block and the patient interface. The air circuit may be referred to as air delivery tube. In some cases there may be separate limbs of the circuit for inhalation and exhalation. In other cases a single limb is used.

Blower or flow generator: A device that delivers a flow of air at a pressure above ambient pressure.

Controller: A device, or portion of a device that adjusts an output based on an input. For example one form of controller has a variable that is under control—the control variable—that constitutes the input to the device. The output of the device is a function of the current value of the control variable, and a set point for the variable. A servo-ventilator may include a controller that has ventilation as an input, a target ventilation as the set point, and level of pressure support as an output. Other forms of input may be one or more of oxygen saturation ($SaO_2$), partial pressure of carbon dioxide ($PCO_2$), movement, a signal from a photoplethysmogram, and peak flow. The set point of the controller may be one or more of fixed, variable or learned. For example, the set point in a ventilator may be a long term average of the measured ventilation of a patient. Another ventilator may have a ventilation set point that changes with time. A pressure controller may be configured to control a blower or pump to deliver air at a particular pressure.

Therapy: Therapy in the present context may be one or more of positive pressure therapy, oxygen therapy, carbon dioxide therapy, control of dead space, and the administration of a drug.

Positive Airway Pressure (PAP) device: A device for providing a supply of air at positive pressure to the airways.

5.6.3 Anatomy of the Face

Ala: the external outer wall or "wing" of each nostril (plural: alar)

Alare: The most lateral point on the nasal ala.

Alar curvature (or alar crest) point: The most posterior point in the curved base line of each ala, found in the crease formed by the union of the ala with the check.

Auricula or Pinna: The whole external visible part of the ear.

(nose) Bony framework: The bony framework of the nose comprises the nasal bones, the frontal process of the maxillae and the nasal part of the frontal bone.

(nose) Cartilaginous framework: The cartilaginous framework of the nose comprises the septal, lateral, major and minor cartilages.

Columella: the strip of skin that separates the nares and which runs from the pronasale to the upper lip.

Columella angle: The angle between the line drawn through the midpoint of the nostril aperture and a line drawn perpendicular to the Frankfurt horizontal while intersecting subnasale.

Frankfort horizontal plane: A line extending from the most inferior point of the orbital margin to the left tragion. The tragion is the deepest point in the notch superior to the tragus of the auricle.

Glabella: Located on the soft tissue, the most prominent point in the midsagittal plane of the forehead.

Lateral nasal cartilage: A generally triangular plate of cartilage. Its superior margin is attached to the nasal bone and frontal process of the maxilla, and its inferior margin is connected to the greater alar cartilage.

Lip, lower (labrale inferius):

Lip, upper (labrale superius):

Greater alar cartilage: A plate of cartilage lying below the lateral nasal cartilage. It is curved around the anterior part of the naris. Its posterior end is connected to the frontal process of the maxilla by a tough fibrous membrane containing three or four minor cartilages of the ala.

Nares (Nostrils): Approximately ellipsoidal apertures forming the entrance to the nasal cavity. The singular form of nares is naris (nostril). The nares are separated by the nasal septum.

Naso-labial sulcus or Naso-labial fold: The skin fold or groove that runs from each side of the nose to the corners of the mouth, separating the cheeks from the upper lip.

Naso-labial angle: The angle between the columella and the upper lip, while intersecting subnasale.

Otobasion inferior: The lowest point of attachment of the auricle to the skin of the face.

Otobasion superior: The highest point of attachment of the auricle to the skin of the face.

Pronasale: the most protruded point or tip of the nose, which can be identified in lateral view of the rest of the portion of the head.

Philtrum: the midline groove that runs from lower border of the nasal septum to the top of the lip in the upper lip region.

Pogonion: Located on the soft tissue, the most anterior midpoint of the chin.

Ridge (nasal): The nasal ridge is the midline prominence of the nose, extending from the Sellion to the Pronasale.

Sagittal plane: A vertical plane that passes from anterior (front) to posterior (rear) dividing the body into right and left halves.

Sellion: Located on the soft tissue, the most concave point overlying the area of the frontonasal suture.

Septal cartilage (nasal): The nasal septal cartilage forms part of the septum and divides the front part of the nasal cavity.

Subalare: The point at the lower margin of the alar base, where the alar base joins with the skin of the superior (upper) lip.

Subnasal point: Located on the soft tissue, the point at which the columella merges with the upper lip in the midsagittal plane.

Supramentale: The point of greatest concavity in the midline of the lower lip between labrale inferius and soft tissue pogonion 5.6.4 Anatomy of the Skull Frontal bone: The frontal bone includes a large vertical portion, the squama frontalis, corresponding to the region known as the forehead.

Mandible: The mandible forms the lower jaw. The mental protuberance is the bony protuberance of the jaw that forms the chin.

Maxilla: The maxilla forms the upper jaw and is located above the mandible and below the orbits. The frontal process of the maxilla projects upwards by the side of the nose, and forms part of its lateral boundary.

Nasal bones: The nasal bones are two small oblong bones, varying in size and form in different individuals; they are placed side by side at the middle and upper part of the face, and form, by their junction, the "bridge" of the nose.

Nasion: The intersection of the frontal bone and the two nasal bones, a depressed area directly between the eyes and superior to the bridge of the nose.

Occipital bone: The occipital bone is situated at the back and lower part of the cranium. It includes an oval aperture, the foramen magnum, through which the cranial cavity communicates with the vertebral canal. The curved plate behind the foramen magnum is the squama occipitalis.

Orbit: The bony cavity in the skull to contain the eyeball.

Parietal bones: The parietal bones are the bones that, when joined together, form the roof and sides of the cranium.

Temporal bones: The temporal bones are situated on the bases and sides of the skull, and support that part of the face known as the temple.

Zygomatic bones: The face includes two zygomatic bones, located in the upper and lateral parts of the face and forming the prominence of the cheek.

5.6.5 Anatomy of the Respiratory System

Diaphragm: A sheet of muscle that extends across the bottom of the rib cage. The diaphragm separates the thoracic cavity, containing the heart, lungs and ribs, from the abdominal cavity. As the diaphragm contracts the volume of the thoracic cavity increases and air is drawn into the lungs.

Larynx: The larynx, or voice box houses the vocal folds and connects the inferior part of the pharynx (hypopharynx) with the trachea.

Lungs: The organs of respiration in humans. The conducting zone of the lungs contains the trachea, the bronchi, the bronchioles, and the terminal bronchioles. The respiratory zone contains the respiratory bronchioles, the alveolar ducts, and the alveoli.

Nasal cavity: The nasal cavity (or nasal fossa) is a large air filled space above and behind the nose in the middle of the face. The nasal cavity is divided in two by a vertical fin called the nasal septum. On the sides of the nasal cavity are three horizontal outgrowths called nasal conchae (singular "concha") or turbinates. To the front of the nasal cavity is the nose, while the back blends, via the choanae, into the nasopharynx.

Pharynx: The part of the throat situated immediately inferior to (below) the nasal cavity, and superior to the oesophagus and larynx. The pharynx is conventionally divided into three sections: the nasopharynx (epipharynx) (the nasal part of the pharynx), the oropharynx (mesopharynx) (the oral part of the pharynx), and the laryngopharynx (hypopharynx).

5.6.6 Materials

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC (included in the range of products sold under this trademark), manufactured by Dow Corning. Another manufacturer of LSR is Wacker. Unless otherwise specified to the contrary, a preferred form of LSR has a Shore A (or Type A) indentation hardness in the range of about 35 to about 45 as measured using ASTM D2240.

Polycarbomate: a typically transparent thermoplastic polymer of Bisphenol-A Carbonate.

5.6.7 Aspects of a Patient Interface

Anti-asphyxia valve (AAV): The component or sub-assembly of a mask system that, by opening to atmosphere in a failsafe manner, reduces the risk of excessive $CO_2$ rebreathing by a patient.

Elbow: A conduit that directs an axis of flow of air to change direction through an angle. In one form, the angle may be approximately 90 degrees. In another form, the angle may be less than 90 degrees. The conduit may have an approximately circular cross-section. In another form the conduit may have an oval or rectangular cross-section.

Frame: Frame will be taken to mean a mask structure that bears the load of tension between two or more points of connection with a headgear. A mask frame may be a non-airtight load bearing structure in the mask. However, some forms of mask frame may also be air-tight.

Functional dead space: The functional dead space refers to at least one region within a breathing circuit where a patient's exhalate may collect such that the normal flow of gas within the breathing circuit cannot effectively flush the exhalate from the breathing circuit.

Headgear: Headgear will be taken to mean a form of positioning and stabilizing structure designed for use on a head. Preferably the headgear comprises a collection of one or more struts, ties and stiffeners configured to locate and retain a patient interface in position on a patient's face for delivery of respiratory therapy. Some ties are formed of a soft, flexible, elastic material such as a laminated composite of foam and fabric.

Membrane: Membrane will be taken to mean a typically thin element that has, preferably, substantially no resistance to bending, but has resistance to being stretched.

Plenum chamber: a mask plenum chamber will be taken to a mean portion of a patient interface having walls enclosing a volume of space, the volume having air therein pressurised above atmospheric pressure in use. A shell may form part of the walls of a mask plenum chamber. In one form, a region of the patient's face forms one of the walls of the plenum chamber.

Seal: The noun form ("a seal") will be taken to mean a structure or barrier that intentionally resists the flow of air through the interface of two surfaces. The verb form ("to seal") will be taken to mean to resist a flow of air.

Shell: A shell will preferably be taken to mean a curved structure having bending, tensile and compressive stiffness, for example, a portion of a mask that forms a curved structural wall of the mask. Preferably, compared to its overall dimensions it is relatively thin. In some forms, a shell may be faceted. Preferably such walls are airtight, although in some forms they may not be airtight.

Stiffener: A stiffener will be taken to mean a structural component designed to increase the bending resistance of another component in at least one direction.

Strut: A strut will be taken to be a structural component designed to increase the compression resistance of another component in at least one direction.

Swivel: (noun) A subassembly of components configured to rotate about a common axis, preferably independently, preferably under low torque. In one form, the swivel may be constructed to rotate through an angle of at least 360 degrees. In another form, the swivel may be constructed to rotate through an angle less than 360 degrees. When used in the context of an air delivery conduit, the sub-assembly of components preferably comprises a matched pair of cylindrical conduits. Preferably there is little or no leak flow of air from the swivel in use.

Tie: A tie will be taken to be a structural component designed to resist tension.

Vent: (noun) the structure that allows a deliberate controlled rate leak of air from an interior of the mask, or conduit to ambient air, to allow washout of exhaled carbon dioxide ($CO_2$) and supply of oxygen ($O_2$).

5.6.8 Terms Used in Relation to Patient Interface

Curvature (of a surface): A region of a surface having a saddle shape, which curves up in one direction and curves down in a different direction, will be said to have a negative curvature. A region of a surface having a dome shape, which curves the same way in two principle directions, will be said to have a positive curvature. A flat surface will be taken to have zero curvature.

Floppy: A quality of a material, structure or composite that is the combination of features of:

Readily conforming to finger pressure.

Unable to retain its shape when caused to support its own weight.

Not rigid.

Able to be stretched or bent elastically with little effort.

The quality of being floppy may have an associated direction, hence a particular material, structure or composite may be floppy in a first direction, but stiff or rigid in a second direction, for example a second direction that is orthogonal to the first direction.

Resilient: Able to deform substantially elastically, and to release substantially all of the energy upon unloading, within a relatively short period of time such as 1 second.

Rigid: Not readily deforming to finger pressure, and/or the tensions or loads typically encountered when setting up and maintaining a patient interface in sealing relationship with an entrance to a patient's airways.

Semi-rigid: means being sufficiently rigid to not substantially distort under the effects of mechanical forces typically applied during positive airway pressure therapy.

5.7 OTHER REMARKS

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being preferably used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a". "an", and "the" include their plural equivalents, unless the context clearly dictates otherwise.

All publications mentioned herein are incorporated by reference to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

Moreover, in interpreting the disclosure, all terms should be interpreted in the broadest reasonable manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular embodiments, it is to be understood that these embodiments are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative embodiments and that other arrangements may be devised without departing from the spirit and scope of the technology.

While the present technology has been described in connection with what are presently considered to be the most practical and preferred examples, it is to be understood that the technology is not to be limited to the disclosed examples, but on the contrary, is intended to cover various modifications and equivalent arrangements included within the spirit and scope of the technology. Also, the various examples described above may be implemented in conjunction with other examples, e.g., aspects of one example may be combined with aspects of another example to realize yet other examples. Further, each independent feature or component of any given assembly may constitute an additional example.

5.8 REFERENCE SIGNS LIST

Number Feature Item
1 neck strap
2 first lower connection portion
2' first lower connection edge portion
3 major side edge
4 first upper connection portion
4' first upper connection edge portion
5 second lower connection portion
5' second lower connection edge portion
6 major side edge
7 second upper connection portion
7' second upper connection edge portion
8 first transitional edge portion
9 second transitional edge portion
10 headgear
12 first minor side edge
13 second minor side edge
14 lateral crown strap
14a connection portion
15 crown assembly
17 lateral crown strap
17a connection portion
18 top crown strap
18a connection portion
19 stepped front side
22 lower mask connection strap
24 upper mask connection strap
25 lower mask connection strap
27 upper mask connection strap
30 fastener member
32 stepped front side
34 smooth front side
100 headgear
102 lateral crown section
102a end portion
104 lateral crown section
104a end portion
106 upper crown section
108 upper mask connection strap
110 lower mask connection strap
115 joint
1000 patient
1100 bed partner
3000 patient interface
3100 seal-forming structure
3200 plenum chamber
3300 positioning and stabilising structure
3400 vent
3500 decoupling structure
3600 connection port
3700 forehead support
4000 PAP device
4010 housing
4012 upper portion
4014 lower portion
4015 panels
4016 chassis
4018 handle
4020 pneumatic block
4100 mechanical and pneumatic components
4112 filter
4142 blower
4170 gas delivery tube/air circuit
4180 gas delivery tube
4190 adaptor
4200 electrical components
4202 PCBA
4210 power supply
4220 input devices
4300 algorithms
5000 humidifier

The invention claimed is:

1. Neck strap for a headgear, comprising:
a one-piece main body adapted to engage a patient's neck, the main body including:
first and second lower connection portions adapted to connect to respective first and second lower mask connection straps, and
first and second upper connection portions adapted to connect to respective first and second lateral crown straps,
wherein the main body comprises two opposing major side edges and two opposing minor side edges that interconnect the opposing major side edges,
wherein the first upper connection portion and the first lower connection portion are located along a first of the two opposing minor side edges, and wherein the second upper connection portion and the second lower connection portion are located along a second of the two opposing minor side edges, and
wherein, in a flat state of the main body, each of the opposing major side edges comprises a curved portion.

2. The neck strap according to claim 1, wherein each curved portion is concave.

3. The neck strap according to claim 1, wherein the neck strap has at least partially a reduced width between the two opposing major side edges in the curved portion.

4. The neck strap according to claim 1, wherein the first and/or second lower connection portion extends parallel to an adjacent portion of the respective minor side edge, and/or wherein the first and/or second upper connection portion extends parallel to an adjacent portion of the respective minor side edge.

5. The neck strap according to claim 4, wherein the first and second upper connection portions and/or the adjacent portions of the minor side edges are adapted to be oriented in an acute angle to a main axis of extension of the respective first and second lateral crown straps.

6. The neck strap according to claim 1, wherein the first and/or second lower connection portion and/or respective portions of the minor side edges is/are adapted to be oriented substantially perpendicular to a main axis of extension of the respective first and/or second lower mask connection strap.

7. The neck strap according to claim 1, wherein the neck strap is symmetrical to a first axis, wherein the first axis in an application position is parallel to the sagittal plane of a patient.

8. The neck strap according to claim 7, wherein the neck strap includes a second axis that extends perpendicular to the first axis.

9. The neck strap according to claim 8, wherein a width perpendicular to the second axis of the neck strap is lowest between the curved portion of the two opposing major side edges of the main body.

10. The neck strap according to claim 1, wherein the major side edges and/or the minor side edges are rounded.

11. A three-dimensionally formed crown strap assembly for a headgear, comprising:
a top crown strap,
first and second lateral crown straps, and
the neck strap according to claim 1.

12. The crown strap assembly according to claim 11, wherein the crown strap assembly has a generally round three-dimensional shape adapted to cup the parietal bone and occipital bone of the patient's head in use.

13. Headgear, comprising:
the crown strap assembly according to claim 11, and
upper mask connection straps.

14. A patient interface for sealed delivery of a flow of breathable gas at a continuously positive pressure with respect to ambient air pressure to an entrance to a patient's airways including at least entrance of a patient's nares, wherein the patient interface is configured to maintain a therapy pressure in a range of about 4 $cmH_2O$ to about 30 $cmH_2O$ above ambient air pressure in use, throughout the patient's respiratory cycle, while the patient is sleeping, to ameliorate sleep disordered breathing;
said patient interface comprising:
a seal-forming structure adapted to form a seal against the patient's airways;
a positioning and stabilising structure to maintain the seal-forming structure in sealing contact with an area surrounding an entrance to the patient's airways while maintaining a therapeutic pressure at the entrance to the patient's airways;
a plenum chamber pressurised at a pressure above ambient pressure in use; and
a gas washout vent configured to allow a flow of patient exhaled $CO_2$ to an exterior of the patient interface to minimise rebreathing of exhaled $CO_2$ by the patient;
wherein the positioning and stabilising structure includes a headgear including a crown strap assembly, first and second upper connection straps provided to the crown strap assembly and adapted to connect to respective upper headgear connectors of the patient interface, and first and second lower connection straps provided to the crown strap assembly and adapted to connect to respective lower headgear connectors of the patient interface, the crown strap assembly including the neck strap according to claim 1, first and second lateral crown straps and a top crown strap adapted to cup the parietal bone and the occipital bone of the patient's head.

15. The neck strap according to claim 1, wherein the main body is adapted to extend in a common plane when laying on a flat surface, and each of the opposing major side edges comprises the curved portion when the neck strap is laying on the flat surface.

16. The neck strap according to claim 1, wherein each of the two opposing major side edges is longer than each of the two opposing minor side edges.

17. The neck strap according to claim 1, wherein a width between the two opposing major side edges in the curved portion is less than a width between the two opposing minor side edges.

* * * * *